US009068985B2

(12) United States Patent
Sjong et al.

(10) Patent No.: US 9,068,985 B2
(45) Date of Patent: Jun. 30, 2015

(54) FLUORESCENT LABELING OF LIVING CELLS

(71) Applicant: Empire Technology Development LLC, Wilmington, DE (US)

(72) Inventors: Angele Sjong, Louisville, CO (US); Kraig Anderson, Burlingame, CA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

(21) Appl. No.: 14/226,398

(22) Filed: Mar. 26, 2014

(65) Prior Publication Data

US 2014/0206840 A1   Jul. 24, 2014

Related U.S. Application Data

(62) Division of application No. 13/824,105, filed as application No. PCT/US2012/032012 on Apr. 3, 2012, now Pat. No. 8,722,354.

(51) Int. Cl.

| G01N 21/64  | (2006.01) |
| G01N 33/569 | (2006.01) |
| A61K 49/00  | (2006.01) |
| C07D 493/10 | (2006.01) |
| C07K 7/00   | (2006.01) |
| C12N 9/00   | (2006.01) |
| G01N 33/533 | (2006.01) |

(52) U.S. Cl.
CPC ...... *G01N 33/56938* (2013.01); *G01N 21/6486* (2013.01); *A61K 49/0041* (2013.01); *C07D 493/10* (2013.01); *C07K 7/00* (2013.01); *C12N 9/00* (2013.01); *G01N 33/533* (2013.01)

(58) Field of Classification Search
None
See application file for complete search history.

(56) References Cited

U.S. PATENT DOCUMENTS

| 4,640,893    | A  | 2/1987  | Mangel et al.  |
| 6,680,195    | B1 | 1/2004  | Patti et al.   |
| 7,534,902    | B2 | 5/2009  | Raines et al.  |
| 2009/0299061 | A1 | 12/2009 | Raines et al.  |

OTHER PUBLICATIONS

Amsberry, K., et al., "Amine prodrugs which utilize hydroxy amide lactonization. II. A potential esterase-sensitive amide prodrug," Pharmaceutical Research, vol. 8, Issue 4, pp. 455-461 (Apr. 1991).
Monera, O. D., et al., "Relationship of sidechain hydrophobicity and alpha-helical propensity on the stability of the single-stranded amphipathic alpha-helix," Journal of Peptide Science, vol. 1, Issue 5, pp. 319-329 (Sep./Oct. 1995).
Nicolaou, M. G., et al., "Phosphate Prodrugs for Amines Utilizing a Fast Intramolecular Hydroxy Amide Lactonization," J. Org. Chem., vol. 61, Issue 24, pp. 8636-8641 (1996).
Sereda, T.J., et al., "Reversed-phase chromatography of synthetic amphipathic alpha-helical peptides as a model for ligand/receptor interactions. Effect of changing hydrophobic environment on the relative hydrophilicity/hydrophobicity of amino acid side-chains," Journal of Chromatography A, vol. 676, Issue 1, pp. 139-153 (Jul. 29, 1994).
Wikipedia, "Foodborne illness," accessed at https://web.archive.org/web/20120229191204/http://en.wikipedia.org/wiki/Foodborne_illness, modified on Feb. 19, 2012, 10 pages.
"Classification of organisms," University of Idaho, Biol 116 presentation, 2008 (retrieved from http://www.webpages.uidaho.edu/bionet/bio1116/O1/presentations.htm on Nov. 11, 2013, 12 pages).
Antos, J., et al., "Site-Specific N- and C-Terminal Labeling of a Single Polypeptide Using Sortases of Different Specifity," J. Am. Chem. Soc., 2009, vol. 131, pp. 10800-10801.
Boekhorst et al. "Genome-Wide Detection and Analysis of Cell Wall-Bound Proteins with LPxTG-Like Sorting Motif," J. Bacteriology, 2005, 187(14), pp. 4928-4934.
Chandler DL, "The Gold Standard for Cell Penetration," Aug. 2013, (MITnews, retrieved from http://web.mit.edu/newsoffice/2013/the-gold-standard-for-cell-penetration-0823.html on Nov. 18, 2013, 2 pages).
Chandran et al. "Latent Fluorophore Based on the Trimethyl Lock," J. Am. Chem. Soc., 2005, vol. 127, pp. 1652-1653.
Fassel et al, "The use of dimethylsulfoxide for fixation of yeasts for electron microscopy," Biotechnic and histochemistry v72(5) 1997, pp. 268-272.
International Search Report and Written Opinion received for PCT/US2012/032012 mailed May 18, 2012.
Jasson, V., et al., "Alternative microbial methods: An overview and selection criteria," Food Microbiology 27 (2010) pp. 710-730.
Lavis et al. "Latent Blue and Red Fluorophores Based on the Trimethyl Lock," ChemBioChem, 2006, vol. 7, 1151-1154.
Lavis, L. et al., "Fluorogenic Label for Biomolecular Imaging," ACS Chemical Biology, 2006, 1(4), pp. 252-260.
Lavis, L. et al., "Synthesis and utility of fluorogenic acetoxymethyl ethers," Chemical Science, 2011, 2(3), pp. 521-530.

(Continued)

*Primary Examiner* — James H Alstrum Acevedo
*Assistant Examiner* — Ronald Niebauer
(74) *Attorney, Agent, or Firm* — Foley & Lardner LLP

(57) ABSTRACT

Latent fluorescent tags, including compounds of Formula I, methods of making latent fluorescent tags, and methods of fluorescently labeling living cells are provided. The compounds of Formula I have the structure:

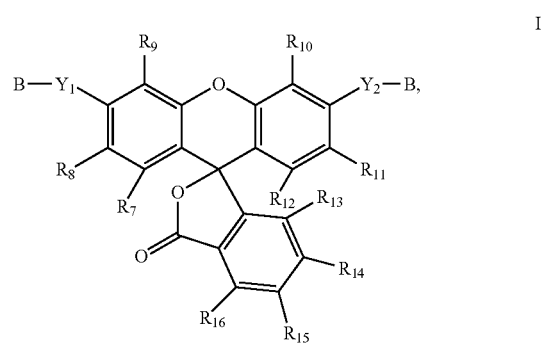

wherein each of the variables are as defined herein.

19 Claims, 9 Drawing Sheets

(56) References Cited

OTHER PUBLICATIONS

Lazcka, O., et al., "Pathogen detection: A perspective of traditional methods and biosensors," Biosensors and Bioelectronics 22, (2007), pp. 1205-1217.

Mangold et al. "Synthesis of Fluorogenic Polymers for Visualizing Cellular Internalization," Organic Letters, 2008, 10(14) pp. 2997-3000.

Nayak, M., et al., "Review: Detection of microorganisms using biosensors—smarter way towards detection techniques," Biosensors and Bioelectronics 25, (2009,) pp. 661-667.

Nelson et al. "Biosynthetic Strategy for Re-engineering the *Staphylococcus aureus* Cell Wall with Nonnative Small Molecules," ACS Chemical Biology, 2010, 5(12), pp. 1147-1155.

Non-Final Office Action in U.S. Appl. No. 13/824,105 dtd Nov. 22, 2013 (11 pages).

Notice of Allowance in U.S. Appl. No. 13/824,105 dtd Feb. 24, 2014 (6 pages).

Popp M., et al., "Sortagging: a versatile method for protein labeling," Nat Chem Biol., 2007, 3(11), pp. 707-708.

Popp, M., et al., "Unit 15.3 Site-Specific Protein Labeling via Sortase-Mediated Transpeptidation," Current Protocols in Protein Science, 2009, pp. 15.3.1-15.3.9.

Proft, T., "Sortase-mediated protein ligation: an emerging biotechnology tool for protein modification and immobilisation," Biotechnol Lett, (2010), vol. 32, pp. 1-10.

Restriction Requirement in U.S. Appl. No. 13/824,105 dtd Oct. 29, 2013 (10 pages).

Wikipedia, The Free Encyclopedia, "Gram-negative Bacteria," retrieved from http://en.wikipedia.org/wiki/Gram-negative, modified on Feb. 24, 2013, 6 pages.

Yamamoto T, and Nagamune T., "Expansion of the sortase-mediated labeling method for site-specific N-terminal labeling of cell surface proteins on living cells," Chem Commun (Camb), (2009), vol. 9, pp. 1022-1024.

FLUORESCENT LABELING OF LIVING CELLS

CROSS-REFERENCE TO RELATED APPLICATIONS

This application is a Divisional under 35 U.S.C. §121 of U.S. patent application Ser. No. 13/824,105, filed Mar. 15, 2013, now U.S. Pat. No. 8,722,354, which claims the benefit under 35 U.S.C. §371 of International Application No. PCT/US2012/032012, filed on Apr. 3, 2012, the entire contents of each are incorporated herein by reference in their entirety for any and all purposes.

SEQUENCE LISTING

The instant application contains a Sequence Listing which has been submitted in ASCII format via EFS-Web and is hereby incorporated by reference in its entirety. Said ASCII copy, created on May 8, 2012, is named 09161906.txt and is 26,718 bytes in size.

FIELD

The present technology relates generally to latent fluorescent tags, methods of making latent fluorescent tags, and methods of fluorescently labeling living cells.

BACKGROUND

The following description is provided to assist the understanding of the reader. None of the information provided or references cited is admitted to be prior art to the present technology.

A variety of food-borne illnesses are caused by bacterial pathogens. Common food pathogens include, for example, *Campylobacter jejuni, Escherichia coli, Salmonella, Listeria monocytogenes, Shigella, Yersinia, Staphylococcus, Clostridium, Vibrio*, and *Bacillus cereus*. Most food pathogens are Gram-positive bacteria which cause a variety diseases and ailments including meningitis (*Listeria, Enterococcus*, and *Streptococcus*); botulism (*Clostridium*), tetanus (*Clostridium*), gas gangrene (*Clostridium*), membranous colitis (*Clostridium*); urinary tract infections (*Enterococcus*), bacteremia (*Enterococcus*), bacterial endocarditis (*Enterococcus*), Sialadenitis, i.e., food poisoning (*Staphylococcus*); strep throat (*Streptococcus*), bacterial pneumonia (*Streptococcus*); anthrax (*Bacillus*), gastroenteritis (*Bacillus*); and diphtheria (*Corynebacterium*).

Pathogens, including food-borne pathogens, may be detected using a variety of biosensing techniques. Typically, biosensors rely on non-covalent binding of a pathogen's surface protein to an antibody to provide specificity. Such immunoassays may be limited, since they are only as effective as the non-covalent binding to the antibody. Typically, antibody binding is coupled with highly sensitive detection methods, such as electrochemical, surface plasmon resonance and piezoelectric-based methods. Alternatively, an enzyme-linked immunosorbent assay (ELISA) may be used to repeatedly cleave a fluorescent tag thereby amplifying the antibody binding event. While antibody binding can be strong, it is non-covalent. Further, a typical bacterial cell includes relatively few binding sites for a selective antibody. Moreover, existing antibody detection schemes react to their binding target regardless of whether the target is part of a live cell. Accordingly, such techniques are prone to false positives and increased background from dead cells and/or cell detritus. Consequently, even with sophisticated detectors, live food pathogen detection limits are still typically high, i.e., approximately $10^4$ to $10^5$ colony forming units per milliliter. Covalent pathogen detection methods that are rapid, sensitive, and specific to live cells, are of interest.

SUMMARY

The present technology generally provides latent fluorescent tags and associated methods for covalently labeling one or more living cells with a fluorescent moiety. Such covalent labeling allows for straight-forward detection, identification, analysis, counting, sorting, and quantification of living cells. In the case of sortase-producing organisms, such as certain bacteria, the latent fluorescent tags of the present technology provide a mechanism for species-specific fluorescent labeling. In comparison to conventional antibody labeling methods, the present latent fluorescent tags are less expensive, easier to synthesize, provide more selective labeling of cells, and are more robust than antibodies. Furthermore, cells labeled using the compounds and methods of the present technology generally yield strong fluorescent signals with minimal background fluorescence, since only living cells fluoresce. The present technology allows for the detection of a broad spectrum of pathogens, including various species of Gram-positive bacteria. The present technology may find particular use in food packaging and monitoring settings, where the presence of such pathogenic bacteria is of concern.

According to one aspect, the present technology provides a compound of Formula I:

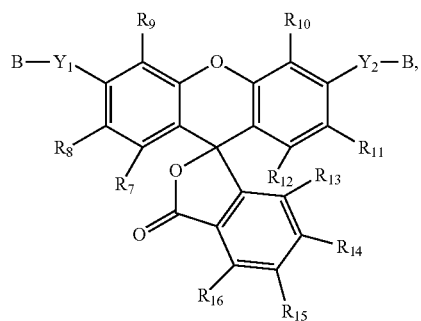

wherein B at each occurrence is independently —CH$_2$OC(O)CH$_3$ or a group of Formula II:

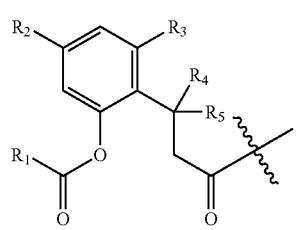

$Y_1$ and $Y_2$ are independently O or NR$_6$; $R_1$, $R_2$, $R_3$, $R_4$, and $R_5$ at each occurrence are independently substituted or unsubstituted C1 to C8 alkyl; R$_6$ at each occurrence is independently H or substituted or unsubstituted C1 to C8 alkyl; $R_7$, $R_8$, $R_9$, $R_{10}$, $R_{11}$, $R_{12}$, $R_{13}$, $R_{14}$, $R_{15}$, $R_{16}$ are independently H, substituted or unsubstituted C1 to C8 alkyl, substituted or unsubstituted C6 to C14 aryl, substituted or unsubstituted C1 to C8 alkoxy, substituted or unsubstituted C6 to C14 aryloxy, hydroxy, halo, nitro, nitrile, amino, amido, imido, urea, amidine, guanidine, enamine, urethane, oxime, hydroxylamine, carboxyl, ester, oxo, thiol, sulfide, sulfoxide, sulfone, sulfonyl, sulfonate, sulfonamide, hydrazine, hydrazide, hydrazone, azide, cyanate, isocyanate, thiocyanate, or isothiocyanate; and one of $R_{13}$, $R_{14}$, $R_{15}$ or $R_{16}$ is a group of Formula III:

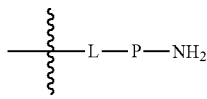

wherein L is a linker selected from the group consisting of substituted or unsubstituted C1 to C30 alkylene and substituted or unsubstituted C1 to C30 heteroalkylene, or is an amino acid linker comprising from 1 to about 20 amino acids; and P is a polypeptide comprising a C-terminus and an N-terminus, wherein the C-terminus of the polypeptide is bonded to the $NH_2$ moiety, and wherein P is cleavable by a sortase enzyme.

In some embodiments of the compound of Formula I, each B is a group of Formula II. In some such embodiments $R_1$ is methyl. In some embodiments, $R_2$, $R_3$, $R_4$, and $R_5$ are each methyl. In some embodiments, $R_1$, $R_2$, $R_3$, $R_4$, and $R_5$ are each methyl.

In some embodiments, $Y_1$ is NH and $Y_2$ is NH. In some embodiments $R_7$, $R_8$, $R_9$, $R_{10}$, $R_{11}$, $R_{12}$, $R_{13}$, $R_{14}$, and $R_{16}$ are each H. In a particular embodiment, each B is a group of Formula II; $R_1$, $R_2$, $R_3$, $R_4$, and $R_5$ are each methyl; $R_7$, $R_8$, $R_9$, $R_{10}$, $R_{11}$, $R_{12}$, $R_{13}$, $R_{14}$, and $R_{16}$ are each H; $Y_1$ is NH; and $Y_2$ is NH.

In some embodiments, the linker L, is an amino acid linker. In some such embodiments, the amino acid linker includes hydrophobic amino acids. In other embodiments, the linker consists of one or more Lys or consists of one or more Gly.

In some embodiments, the linker L is a substituted or unsubstituted C1 to C30 alkylene linker. In some such embodiments, the linker is a substituted or unsubstituted C1 to C10 alkylene linker.

In some embodiments, the linker L is a substituted or unsubstituted C1 to C30 heteroalkylene linker. In some such embodiments, the linker is a substituted or unsubstituted C1 to C10 heteroalkylene linker. In some embodiments, the linker is a substituted or unsubstituted poly(oxyalkylene) wherein the alkylene is a C2 to C10 alkylene. In some embodiments, the linker is poly(oxyethylene).

In some embodiments, the linker includes one or more functional groups selected from the group consisting of carbonyls, esters, amides, ethers, amines, imines, urethanes, imides, sulfoxides, sulfones, sulfonamides, and disulfides.

In some embodiments, the linker is covalently attached to both P and the compound of Formula I through amide functional groups. In some embodiments, the linker is covalently attached to P through a disulfide bond.

In some embodiments, P is a pentapeptide or a hexapeptide. In some embodiments, P is a group of Formula IV:

Xaa$_1$-Xaa$_2$-Xaa$_3$-Xaa$_4$-Xaa$_5$ (SEQ ID NO: 1)   IV wherein: Xaa$_1$ is an amino acid selected from the group consisting of L, N, A, I, G, V, P, F, and Y; Xaa$_2$ is an amino acid selected from the group consisting of P, S, E, G, K, A, D, V, and L; Xaa$_3$ is an amino acid selected from the group consisting of K, A, N, Q, E, T, P, S, H, D, I, R, V, M, F, L, Y, and G;

Xaa$_4$ is an amino acid selected from the group consisting of T, A, K, G, S, Y, E, M, V, and L; and Xaa$_5$ is an amino acid selected from the group consisting of G, A, S, D, N, V, Q, E, K and P.

In some embodiments the compound of Formula I is a compound of Formula IA:

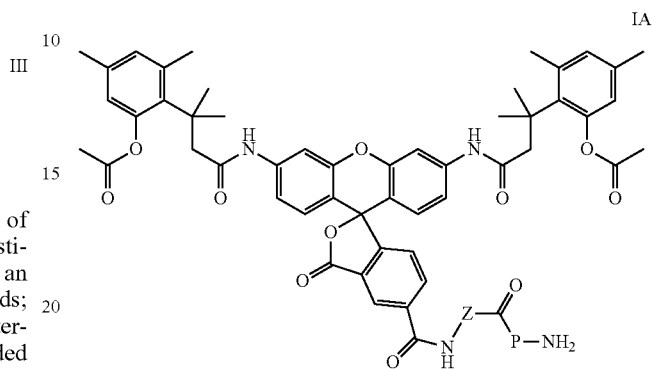

wherein Z is selected from the group consisting of substituted or unsubstituted C1 to C10 alkylene and substituted or unsubstituted C1 to C10 heteroalkylene, or when taken together with the NH and C=O moieties bonded thereto is an amino acid linker comprising from 1 to about 20 amino acids.

According to another aspect, the present technology provides a method of labeling a living cell, the method comprising contacting at least one living cell with a compound of Formula I:

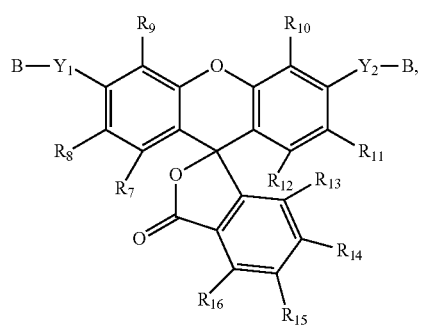

wherein B at each occurrence is independently —CH$_2$OC(O)CH$_3$ or a group of Formula II:

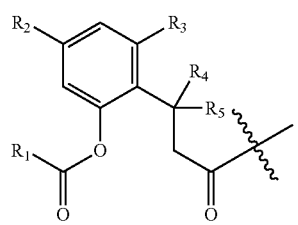

$Y_1$ and $Y_2$ are independently O or NR$_6$; $R_1$, $R_2$, $R_3$, $R_4$, and $R_5$ at each occurrence are independently substituted or unsubstituted C1 to C8 alkyl; $R_6$ at each occurrence is independently H or substituted or unsubstituted C1 to C8 alkyl; $R_7$, $R_8$, $R_9$, $R_{10}$, $R_{11}$, $R_{12}$, $R_{13}$, $R_{14}$, $R_{15}$, $R_{16}$ are independently H, substituted or unsubstituted C1 to C8 alkyl, substituted or unsubstituted C6 to C14 aryl, substituted or unsubstituted C1 to C8 alkoxy, substituted or unsubstituted C6 to C14 aryloxy, hydroxy, halo, nitro, nitrile, amino, amido, imido, urea, amidine, guanidine, enamine, urethane, oxime, hydroxylamine, carboxyl, ester, oxo, thiol, sulfide, sulfoxide, sulfone, sulfonyl, sulfonate, sulfonamide, hydrazine, hydrazide, hydrazone, azide, cyanate, isocyanate, thiocyanate, or isothiocyanate; and one of $R_{13}$, $R_{14}$, $R_{15}$ or $R_{16}$ is a group of Formula III:

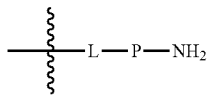
III wherein L is a linker selected from the group consisting of substituted or unsubstituted C1 to C30 alkylene and substituted or unsubstituted C1 to C30 heteroalkylene, or is an amino acid linker comprising from 1 to about 20 amino acids; and P is a polypeptide comprising a C-terminus and an N-terminus, wherein the C-terminus of the polypeptide is bonded to the $NH_2$ moiety, and wherein P is cleavable by a sortase enzyme.

In some embodiments of the compound of Formula I, each B is a group of Formula II. In some such embodiments $R_1$ is methyl. In some embodiments, $R_2$, $R_3$, $R_4$, and $R_5$ are each methyl. In some embodiments, $R_1$, $R_2$, $R_3$, $R_4$, and $R_5$ are each methyl.

In some embodiments, $Y_1$ is NH and $Y_2$ is NH. In some embodiments $R_7$, $R_8$, $R_9$, $R_{10}$, $R_{11}$, $R_{12}$, $R_{13}$, $R_{14}$, and $R_{16}$ are each H. In a particular embodiment, each B is a group of Formula II; $R_1$, $R_2$, $R_3$, $R_4$, and $R_5$ are each methyl; $R_7$, $R_8$, $R_9$, $R_{10}$, $R_{11}$, $R_{12}$, $R_{13}$, $R_{14}$, and $R_{16}$ are each H; $Y_1$ is NH; and $Y_2$ is NH.

In some embodiments, the linker L, is an amino acid linker. In some such embodiments, the amino acid linker includes hydrophobic amino acids. In other embodiments, the linker consists of one or more Lys or consists of one or more Gly.

In some embodiments, the linker L is a substituted or unsubstituted C1 to C30 alkylene linker. In some such embodiments, the linker is a substituted or unsubstituted C1 to C10 alkylene linker.

In some embodiments, the linker L is a substituted or unsubstituted C1 to C30 heteroalkylene linker. In some such embodiments, the linker is a substituted or unsubstituted C1 to C10 heteroalkylene linker. In some embodiments, the linker is a substituted or unsubstituted poly(oxyalkylene) wherein the alkylene is a C2 to C10 alkylene. In some embodiments, the linker is poly(oxyethylene).

In some embodiments, the linker includes one or more functional groups selected from the group consisting of carbonyls, esters, amides, ethers, amines, imines, urethanes, imides, sulfoxides, sulfones, sulfonamides, and disulfides.

In some embodiments, the linker is covalently attached to both P and the compound of Formula I through amide functional groups. In some embodiments, the linker is covalently attached to P through a disulfide bond.

In some embodiments, P is a pentapeptide or a hexapeptide.

In some embodiments the compound of Formula I is a compound of Formula IA:

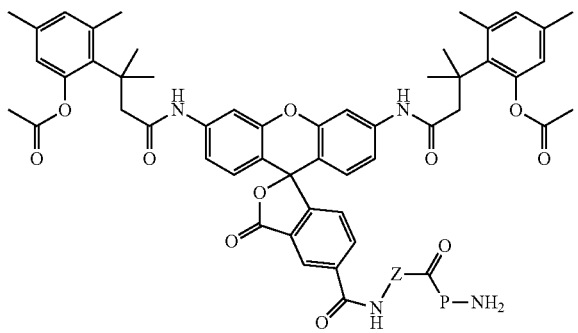

wherein Z is selected from the group consisting of substituted or unsubstituted C1 to C10 alkylene and substituted or unsubstituted C1 to C10 heteroalkylene, or when taken together with the NH and C=O moieties bonded thereto is an amino acid linker comprising from 1 to about 20 amino acids.

In some embodiments, the living cell produces a sortase enzyme.

In some embodiments, the living cell is a Gram-positive bacterium. In some such embodiments, the Gram-positive bacterium is from a genus selected from the group consisting of Clostridium, Enterococcus, Staphylococcus, Streptococcus, Actinobacter, Bacillus, Listeria, and Corynebacterium.

In some embodiments, the compound of Formula I or a metabolite thereof is covalently bound to the living cell after the contacting step.

In some embodiments, the at least a portion of the living cell exhibits increased fluorescence after the contacting step compared to before the contacting step.

In some embodiments, the method further comprises detecting fluorescence of the cell after the contacting step.

The foregoing summary is illustrative only and is not intended to be in any way limiting. In addition to the illustrative aspects, embodiments and features described above, further aspects, embodiments and features will become apparent by reference to the following drawings and the detailed description.

BRIEF DESCRIPTION OF THE DRAWINGS

FIG. 2 discloses SEQ ID NO: 2.

FIG. 4 discloses SEQ ID NOS 2 and 72, respectively, in order of appearance.

FIG. 4 discloses SEQ ID NO: 2 and SEQ ID NO: 72, respectively, in order of appearance.

FIG. 9 discloses both sequences as SEQ ID NO: 122.

DETAILED DESCRIPTION

Figure 1:
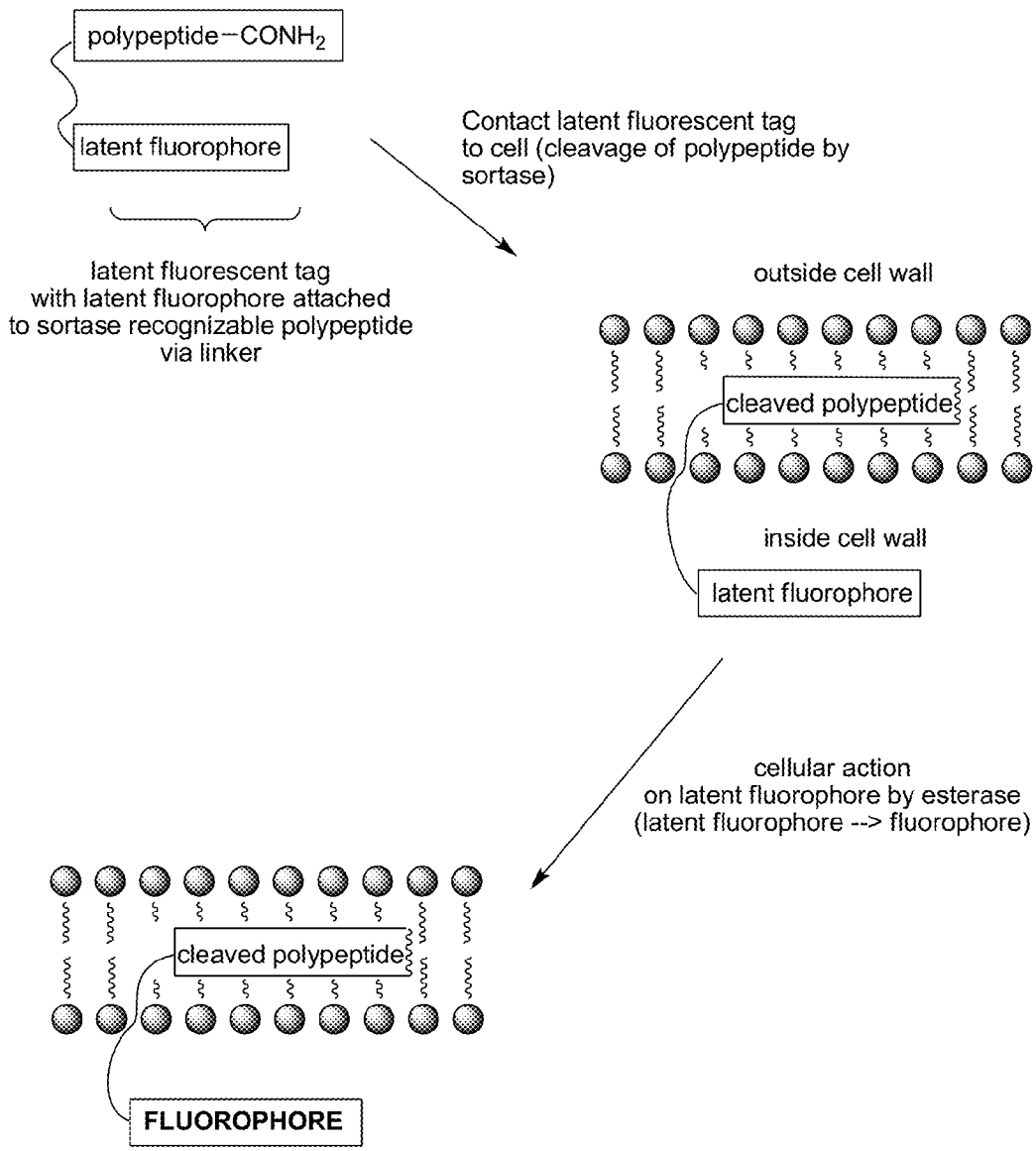
FIG. 1 is a schematic illustration of the labeling of a live cell with a latent fluorescent tag of the present technology, according to one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here.

The technology is described herein using several definitions, as set forth throughout the specification.

The use of the terms "a" and "an" and "the" and similar referents in the context of describing the elements (especially in the context of the following claims) are to be construed to cover both the singular and the plural, unless otherwise indicated herein or clearly contradicted by context.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

In general, "substituted" refers to a group, as defined below (e.g., an alkyl or aryl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents.

Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls(oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Alkyl groups include straight chain and branched alkyl groups having from 1 to 20 carbon atoms or, in some embodiments, from 1 to 12, 1 to 8, 1 to 6, or 1 to 4 carbon atoms. Alkyl groups further include cycloalkyl groups. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above. For example, the term haloalkyl refers to an alkyl group substituted with one or more halogen atoms.

Alkenyl groups include straight and branched chain and cycloalkyl groups as defined above, except that at least one double bond exists between two carbon atoms. Thus, alkenyl groups have from 2 to about 20 carbon atoms, and typically from 2 to 12 carbons or, in some embodiments, from 2 to 8, 2 to 6, or 2 to 4 carbon atoms. In some embodiments, alkenyl groups include cycloalkenyl groups having from 4 to 20 carbon atoms, 5 to 20 carbon atoms, 5 to 10 carbon atoms, or even 5, 6, 7, or 8 carbon atoms. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl, among others. Representative substituted alkenyl groups may be mono-substituted or substituted more than once, such as, but not limited to, mono-, di- or tri-substituted with substituents such as those listed above.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8, 2 to 6, or 2 to 4 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 20 carbon atoms, 7 to 14 carbon atoms or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-ethyl-indanyl. Representative substituted aralkyl groups may be substituted one or more times with substituents such as those listed above.

Alkoxy and aryloxy groups are hydroxyl groups (—OH) in which the bond to the hydrogen atom is replaced by a bond to a carbon atom of an alkyl group or aryl group, respectively, as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of aryloxy groups include but are not limited to phenoxy, naphthyloxy, and the like. Representative substituted alkoxy groups or aryloxy groups may be substituted one or more times with substituents such as those listed above.

The term "halogen" (or "halo") refers to —F, —Cl, —Br, or —I groups.

The term "hydroxyl" (or "hydroxy") refers to —OH groups.

The term "cyano" (or "nitrile") refers to —CN groups.

The term "ester" as used herein refers to —COOR groups, where R is a substituted or unsubstituted alkyl, alkenyl, alkynyl, or aryl group as defined herein.

The term "amine" (or "amino") as used herein refers to —NHR and —NRR' groups, wherein R, and R are independently hydrogen, or a substituted or unsubstituted alkyl, alkenyl, alkynyl, aryl, or aralkyl group as defined herein. Non-limiting examples of amine groups include, but are not limited to, —NH$_2$, methylamino, dimethylamino, ethylamino, diethylamino, propylamino, isopropylamino, phenylamino, benzylamino, and the like.

As used herein, "poly(oxyalkylene)" refers to groups having the structure -(alkylene-O)$_n$- where n is an integer such as 1, 2, 3, 4, 5, 6, 7, 8, 9, 10, 15, 20, 50, 100, or an integer larger than 100. Examples of poly(oxyalkylene) groups include, but are not limited to poly(oxyethylene), poly(oxypropylene), poly(oxybutylene), and others.

As used herein, the term "Gram-positive bacteria" and grammatical forms thereof refers to bacteria, which have been classified using the Gram stain as having a blue stain. Gram-positive bacteria have a thick cell membrane including multiple layers of peptidoglycan and an outside layer of teichoic acid. Examples of genera of Gram-positive bacteria include, but are not limited to, *Clostridium, Enterococcus, Staphylococcus, Streptococcus, Actinobacter, Bacillus, Listeria*, and others.

As used herein, the term "sortase" or "sortase enzyme" refers to a prokaryotic enzyme having a catalytic domain with activity capable of selectively cleaving a backbone peptide bond of a polypeptide at a sortase recognition sequence and catalyzing a transpeptidation reaction which results in the formation of an amide bond between the terminal carboxyl group created by the cleavage and a surface protein of the cell wall of a cell. Sortase is present in almost all Gram-positive bacteria, as well as a few Gram-negative bacteria and *Archaea*. The expression "cleavable by a sortase enzyme" refers to a polypeptide which includes a sortase recognition sequence capable of being cleaved and covalently attached to a surface protein of the cell wall of a cell by a sortase enzyme.

The term "polypeptide" or "peptide" as used herein refers to two or more amino acids linked by a peptide (i.e., amide) bond between the carboxyl terminus of one amino acid and the amino terminus of another. The term "polypeptide" or "peptide" includes a protein. Where the polypeptide includes a sortase recognition sequence, the polypeptide may be cleave by a sortase enzyme in the manner described above. The term "peptide" may be combined with a prefix indicating the number of amino acids in the peptide, e.g., a "pentapeptide" is a peptide of five amino acids.

The term "amino acid" is art recognized and generally refers to a natural or unnatural alpha or beta amino acid. The term "amino acid" includes, but is not limited to, the twenty standard L-amino acids commonly found in naturally occurring peptides. Natural or unnatural amino acids may be optionally substituted by one to four substituents, such those described herein.

The term "fluorescent" and grammatical forms thereof is art recognized and generally refers to the property of a molecule whereby, upon irradiation with light of a given wavelength or wavelengths, the molecule becomes excited and emits light of a longer wavelength or wavelengths. The term "fluorophore" as used herein refers to a fluorescent molecule or a portion of a molecule which gives rise to fluorescent properties. There are a number of parameters which together describe the fluorescence characteristics of a fluorophore. These include, for example, characteristic wavelengths, such as the wavelengths of excitation and emission maxima, the breadth of the peaks for excitation and emission, the difference between the excitation and emission maxima (the "Stokes shift"), fluorescence intensity, quantum yield, and extinction coefficient. For biological or biochemical applications, longer Stokes shifts are generally preferred to shorter ones. Fluorescence intensity is determined as the product of the extinction coefficient and the fluorescence quantum yield. The fluorescence quantum yield is a measure of the relative efficiency or extent to which light energy absorbed is re-emitted as fluorescence. It is defined as the ratio of the number of fluorescence photons emitted, F to the number of photons absorbed, A, and molecules with larger quantum yields exhibit greater fluorescence intensity.

The molar extinction coefficient is a measure of a fluorophore's ability to absorb light. Commonly used fluorophores tend to have molar extinction coefficients (at their absorption maximum) between 5,000 and 200,000 cm$^{-1}$ M$^{-1}$. Because fluorescence intensity is the product of quantum yield and the extinction coefficient, higher extinction coefficients also correlate with greater fluorescence intensity.

The present technology generally provides latent fluorescent tags and associated methods for covalently labeling one or more living cells with a fluorescent moiety, i.e., a fluorophore. In one embodiment, the technology is broadly illustrated in FIG. 1. As shown in FIG. 1, a latent fluorescent tag of the present technology generally includes a latent fluorophore attached to a polypeptide via a linker. The polypeptide attached via its N-terminus to the linker and the C-terminus of the polypeptide is an amide group. The polypeptide of the latent fluorescent tag includes a sortase recognition sequence which is recognizable by a sortase enzyme of a cell. When the latent fluorescent tag is contacted with the cell, the sortase enzyme of the cell cleaves the polypeptide, covalently attaching the remainder of the latent fluorescent tag to the cell wall of the cell via the cleaved polypeptide residue. Cellular action by esterase, present in the interior of the cell, converts (i.e., activates) the latent fluorophore portion of the latent fluorescent tag into a fluorescent moiety. The tethered fluorescent moiety remains covalently attached to the cell wall, thus permitting individual cell counting and/or imaging of live cells. Although the fluorophore and latent fluorophore moieties are depicted as located in the interior of the cell in FIG. 1, the linker may be of sufficient length to allow the fluorophore or latent fluorophore to transit the cell wall, such that the fluorophore or latent fluorophore may be located internally or externally to the cell. Notably, the latent fluorescent tags of the present technology are specific to live cells for one or more of the following reasons. Typically, the action of the sortase enzyme in cleaving the polypeptide and covalently attaching the remainder of the tag to the cell via the cleaved polypeptide residue occurs only in live cells. Further, the esterase needed for activation of the latent fluorophore typically occurs with significant activity only in live cells. Furthermore, high fluorescence signals with low background may be obtained, since the latent fluorescent tags of the present technology are minimally or non-fluorescent until covalent attachment and activation. Additionally, the latent fluorescent tags of the present technology may include multiple (latent) fluorophores for obtaining even higher fluorescence signals. In comparison to contemporary antibody-based labeling methods, the present latent fluorescent tags are more cost-effective, more robust, and more reactive (i.e., thousands of tags may bind to a single cell).

Figure 2:
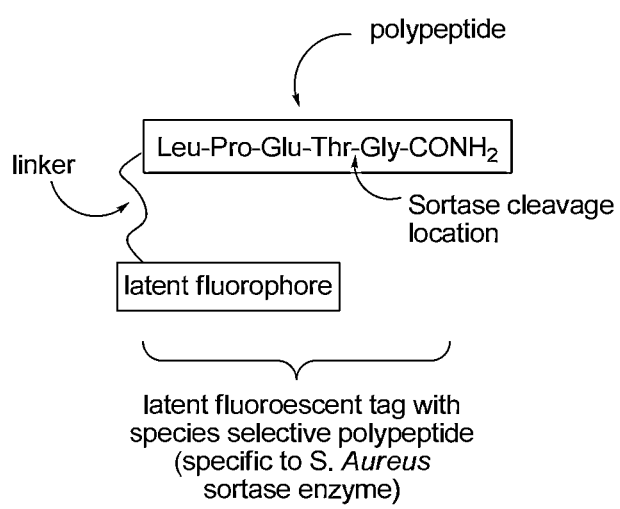
FIG. 2 is an illustration of a latent fluorescent tag of the present technology which is selective to Staphylococcus Aureus (S. Aureus), according to one embodiment.

Using the present technology, various types of living cells may be selectively labeled, including, e.g., a bacterium cell, such as a cell of a Gram-positive bacterium. The specificity in labeling of the present methods takes advantage of the fact that certain species of bacteria express sortase enzymes which recognize specific polypeptide sequences. Accordingly, the polypeptide portion of the latent fluorescent tags of the present technology may be tailored such that they are recognized by only a specific species of bacteria. In this regard, it is possible to selectively label (and thus identify) certain species of bacteria in the presence of others. For example, FIG. 2 illustrates one embodiment of this concept with regard to selective labeling of S. Aureus. As shown in FIG. 2, one embodiment of the latent fluorescent tag includes the polypeptide Leu-Pro-Glu-Thr-Gly (SEQ ID NO: 2), a sequence which is recognized by S. Aureus. The C-terminus of the polypeptide (i.e., Gly) is in the form of an amide, while the N-terminus is attached to the latent fluorophore via the linker. The sortase enzyme of S. Aureus cleaves the polypeptide between the Thr and Gly residues of the polypeptide, and covalently anchors the remaining N-terminal portion of the polypeptide (along with the linker and latent fluorophore) to the cell wall of S. Aureus. In an analogous fashion as shown in FIG. 1, activation of the latent fluorophore by cellular esterase accomplishes the selective fluorescent labeling of a S. Aureus cell. Other species of bacteria may be selectively and covalently labeled by selecting a polypeptide moiety that is recognized by a sortase specific to the bacteria species of interest.

In some embodiments, the latent fluorescent tags of the present technology may be used to detect the presence of bacterial pathogens in various food products for human or other animal consumption. For instance, the present latent fluorescent tags may be used to detect the presence of bacterial pathogens in (or on) fruits, vegetables, cereals, grains, meat, dairy products, animal feed, and other consumables. Common bacterial pathogens which may be detected by the present technology include, but are not limited to, *Campylobacter* (e.g., *Campylobacter jejuni*), *Escherichia coli*, *Salmonella*, *Listeria* (e.g., *L. monocytogenes*), *Shigella*, *Yersinia*, *Staphylococcus*, *Streptococcus*, *Clostridium*, *Vibrio*, *Enterococcus*, *Bacillus* (e.g., *B. cereus* and *B. anthracis*), *Actinobacter*, and *Cornyebacterium*. In some embodiments, the latent fluorescent tags of the present technology are used to detect a Gram-positive bacterium from any of the following genera: *Clostridium, Enterococcus, Staphylococcus, Streptococcus, Actinobacter, Bacillus,* and *Listeria*.

According to one aspect, the present technology provides a compound of Formula I:

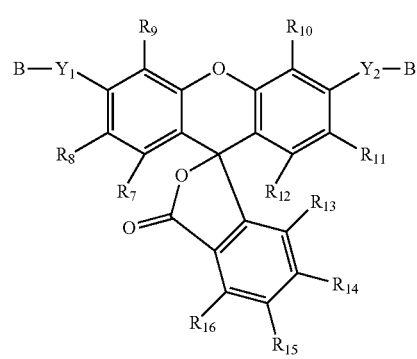

wherein B at each occurrence is independently —CH$_2$OC(O)CH$_3$ or a group of Formula II:

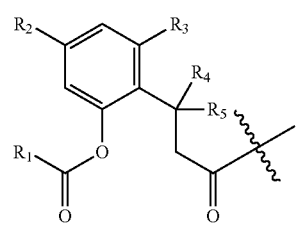

Y$_1$ and Y$_2$ are independently O or NR$_6$; R$_1$, R$_2$, R$_3$, R$_4$, and R$_5$ at each occurrence are independently substituted or unsubstituted C1 to C8 alkyl; R$_6$ at each occurrence is independently H or substituted or unsubstituted C1 to C8 alkyl; R$_7$, R$_8$, R$_9$, R$_{10}$, R$_{11}$, R$_{12}$, R$_{13}$, R$_{14}$, R$_{15}$, R$_{16}$ are independently H, substituted or unsubstituted C1 to C8 alkyl, substituted or unsubstituted C6 to C14 aryl, substituted or unsubstituted C1 to C8 alkoxy, substituted or unsubstituted C6 to C14 aryloxy, hydroxy, halo, nitro, nitrile, amino, amido, imido, urea, amidine, guanidine, enamine, urethane, oxime, hydroxylamine, carboxyl, ester, oxo, thiol, sulfide, sulfoxide, sulfone, sulfonyl, sulfonate, sulfonamide, hydrazine, hydrazide, hydrazone, azide, cyanate, isocyanate, thiocyanate, or isothiocyanate; and one of R$_{13}$, R$_{14}$, R$_{15}$ or R$_{16}$ is a group of Formula III:

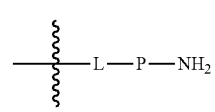

wherein, L is a linker selected from the group consisting of substituted or unsubstituted C1 to C30 alkylene and substituted or unsubstituted C1 to C30 heteroalkylene, or is an amino acid linker comprising from 1 to about 20 amino acids; and P is a polypeptide comprising a C-terminus and an N-terminus, wherein the C-terminus of the polypeptide is bonded to the NH$_2$ moiety, and wherein P is cleavable by a sortase enzyme.

The compound of Formula I includes a number of structural features, including a polypeptide, a linker, a latent fluorophore, and blocking groups. The polypeptide is cleavable by the sortase enzyme of a cell. In this regard, the polypeptide includes a sortase recognition sequence allowing for cleavage by sortase and subsequent attachment of the remaining portion of the compound of Formula I to the cell wall of the cell. The polypeptide is attached to the latent fluorophore via a linker. The latent fluorophore is non- or minimally fluorescent by virtue of its attachment to the blocking groups. Upon cleavage of the blocking groups in the living cellular environment, e.g., by an esterase, the latent fluorophore portion of the latent fluorescent tag is converted to a fluorescent moiety. Each of these structural features is discussed below.

Upon activation, the latent fluorophore portion of the compound of Formula I serves as a reporter group whose presence can be detected by its light absorbing or light emitting properties, and in particular, its fluorescence properties. In this regard, after labeling living cells with the compound of Formula I, such cells may be detected via their fluorescence, allowing for their identification and quantification. As will be appreciated by those of the skill in the art, the latent fluorophore portion of the compound of Formula I is derived from certain classes of fluorescent dyes such as fluorescein or rhodamine dyes. The syntheses of numerous derivatives of fluorescein and rhodamine dyes have been reported and many such dyes are commercially available. Furthermore, the substitution pattern about rhodamine or fluorescein dye portion may be varied as to tailor the fluorescence properties of latent fluorescent tags prepared therefrom. For example, substitution of a fluorescein or rhodamine dye with electron withdrawing or donating groups may provide a dye which fluoresces at a different wavelength from that of parent, unsubstituted dye. Additionally, many rhodamine and fluorescein dye derivatives include reactive groups to which the Sortase-cleavable polypeptide may be attached directly or indirectly, as will be further detailed herein. Examples of suitable reactive groups for direct or indirect attachment of the polypeptide include, but are not limited to, carboxylic acids, esters (including activated esters such as N-hydroxysuccinimidyl esters), alcohols, thiols, amines, halides, sulfonyl halides, azides, alkynes, isothiocyanates, isocyanates, maleimides, methanesulfonothionates (i.e., CH$_3$SO$_2$S— groups), and the like. Such reactive groups may be attached the dye directly, or otherwise tethered to the dye. The present technology contemplates of any type of rhodamine or fluorescein dye or their derivatives. Examples of suitable rhodamine and fluorescein dyes include, but are not limited to those indicated in FIG. 3 (commercially available from Molecular Probes (Eugene, Oreg.) or Biotium (Hayward, Calif.)).

Figure 4:
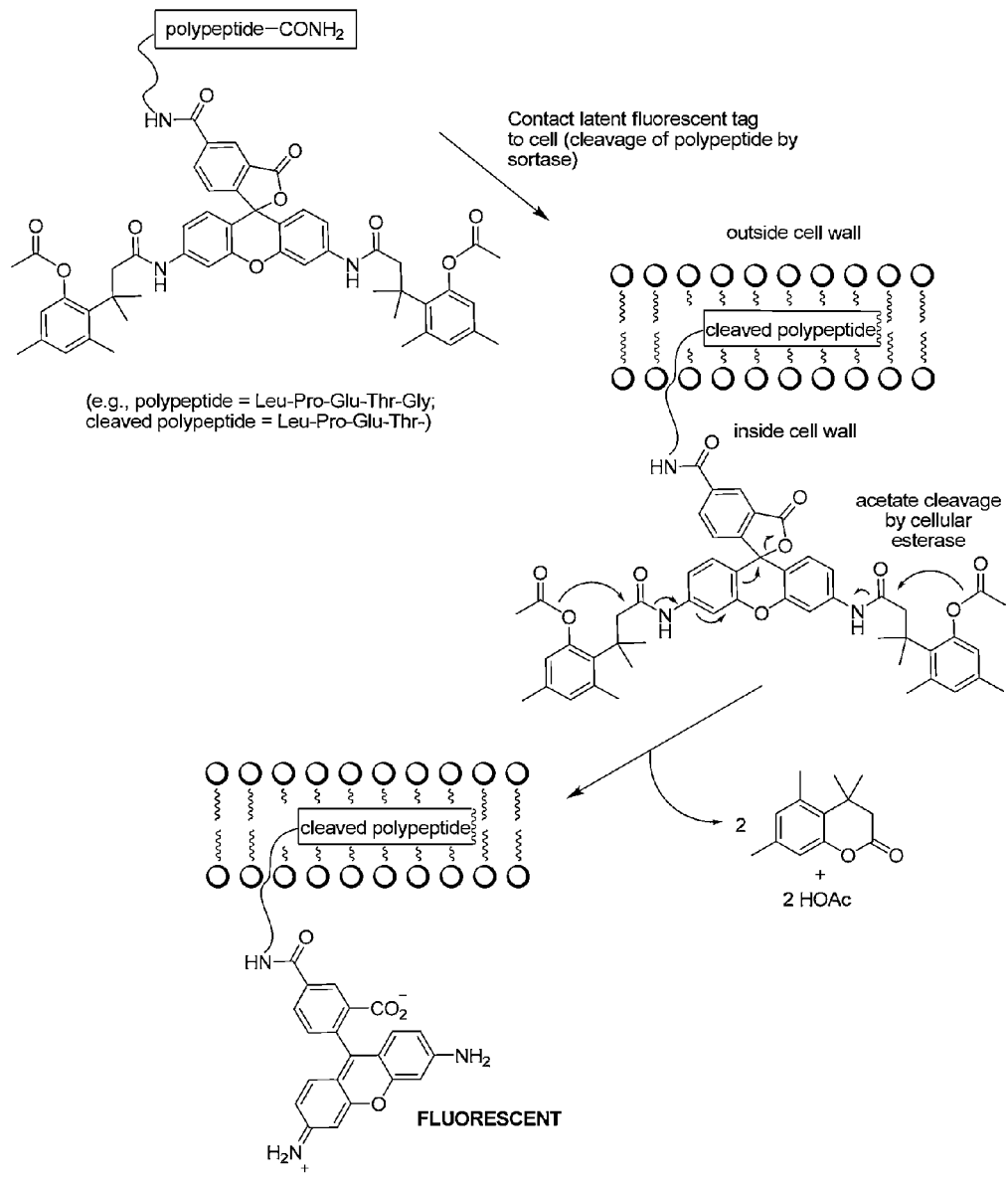
FIG. 4 is a schematic illustration of the fluorescent labeling of a live cell with a latent fluorescent tag including a rhodamine dye portion and trimethyl lock blocking groups, according to one embodiment.

The blocking groups, B, in the compound of Formula I are independently and at each occurrence —CH$_2$OC(O)CH$_3$ or a group of Formula II. In some embodiments, the group of Formula II is a 3-(2-acetoxy-4,6-dimethylphenyl)-3-methylbutanoyl ("trimethyl lock") group. The blocking groups render the latent fluorophore portion of the latent fluorescent tag non- or minimally fluorescent. However, in the living cellular environment, the blocking groups may be cleaved rendering a fluorescent cleavage product. In this regard, the blocking groups, which include ester linkages, may be cleaved in the cellular environment by esterase enzymes. A non-limiting illustration of this concept, based on trimethyl lock blocking groups and a rhodamine dye, is shown in FIG. 4. As previously set forth, when the latent fluorescent tag is contacted with the living cell, the sortase enzyme of the cell cleaves the polypeptide residue, covalently attaching the remainder of the latent fluorescent tag to the cell wall of the cell via the cleaved polypeptide residue. The trimethyl lock blocking groups of the latent fluorescent tag possess unfavorable steric interactions between neighboring methyl groups. Thus, enzymatic cleavage of the acetate groups of one or both of the trimethyl lock blocking groups results the rapid expulsion of 4,4,5,7-tetramethylchroman-2-one with concomitant unmasking of the latent fluorophore. In this manner, the cell is covalently labeled with a fluorescent tag. Blocking groups of Formula II (including trimethyl lock groups) and —CH$_2$OC(O)CH$_3$ (i.e., acetoxymethyl ether blocking groups) generally display remarkable stability in aqueous solution yet rapidly release fluorescent compounds attached thereto upon exposure to esterase. Strategies employing trimethyl lock and acetoxymethyl ether blocking groups with fluorescent compounds, including fluorescein and rhodamine dyes, have been described by: Raines, R. et al., U.S. Pat. No. 7,534,902; Chandran, S. et al., J. Am. Chem. Soc. 2005, 127, 1652-1653; Lavis, L. et al., Chem. Sci., 2011, 2, 521-530; and Lavis, L. et al., ChemBioChem 2006, 7, 1151-1154; Mangold, S. et al., Org. Lett 2008, 10(14), 2997-3000.

The latent fluorescent tags of the present technology include a polypeptide which is recognized and cleaved by a sortase enzyme, thus providing a mechanism for the covalent labeling of a cell. Sortase enzymes are transpeptidases produced by Gram-positive bacteria (as well as a few Gram-negative bacteria and *Archaea*) to anchor cell surface proteins covalently to the cell wall. For example, a sortase enzyme from *S. aureus* cleaves the sortase recognition sequence LPXTG (SEQ ID NO: 3) between the Gly and Thr residues and catalyzes the formation of an amide bond between the carboxyl-group of Thr and an amino group of the cell wall peptidoglycan. (As will be understood by those of skill in the art, the one and three letter codes for L-alpha amino acids used throughout this disclosure are well known in the art and have their art-accepted meanings.) The sortase recognition sequence is referred to as "LPXTG" (SEQ ID NO: 3), based on the main conserved residues: Leu, Pro, Thr, and Gly; X may be any naturally occurring amino acid residue. Not all polypeptides which have been experimentally verified to be substrates for sortase enzymes fit the canonical motif of LPXTG (SEQ ID NO: 3). Numerous sortase recognition sequences other than LPXTG (SEQ ID NO: 3) are known in the art. For example, the sortase SrtB from *S. aureus* recognizes the sequence NPQTN (SEQ ID NO: 4). In some cases, the sortase recognition sequence includes six or more amino acid residues, such as LPQTXE (SEQ ID NO: 5) which is a predicted sortase substrate for *Lactobacillus plantarum*.

Boekhorst et al., (J. Bacteriology, 2005, 187(14), 4928-4934), have predicted numerous pentapeptide sortase recognition sequences using in silico analysis of 199 sequenced prokaryote genomes. Such studies have described species-specific polypeptides for a wide range of Gram-positive bacteria, including food pathogens and other pathogens of interest. In particular, species-specific pentapeptides were predicted for: *Bacillus anthracis* A2012, *Bacillus anthracis* Ames, *Bacillus anthracis* Ames 0581, *Bacillus anthracis* str Sterne, *Bacillus cereus* ATCC14579, *Bacillus cereus* ATCC 10987, *Bacillus cereus* ZK, *Bacillus halodurans*, *Bacillus lichenifonnis* ATCC 14580, *Bacillus lichenifonnis* DSM 13, *Bacillus subtilis*, *Bacillus thuringiensis konkukian*, *Bifidobacterium longum*, *Bradyrhizobium japonicum*, *Clostridium* acetobutylicum, *Clostridium perfringens*, *Clostridium tetani* E88, *Corynebacterium diphtheriae*, *Enterococcus faecalis* V583, *Lactobacillus johnsonii* NCC 533, *Lactobacillus plantarum*, *Lactococcus lactis*, *Listeria innocua*, *Listeria monocytogenes*, *Listeria monocytogenes* 4b F2365, *Methanopyrus kandleri*, *Oceanobacillus iheyensis*, *Shewanella oneidensis*, *Staphylococcus aureus* MW2, *Staphylococcus aureus* Mu50, *Staphylococcus aureus* N315, *Staphylococcus aureus aureus* MRSA252, *Staphylococcus aureus* aureus MSSA476, *Staphylococcus epidermidis* ATCC 12228, *Streptococcus agalactiae* 2603, *Streptococcus agalactiae* NEM316, *Streptococcus mutans*, *Streptococcus pneumoniae* R6, *Streptococcus pneumoniae* TIGR4, *Streptococcus pyogenes*, *Streptococcus pyogenes* MGAS10394, *Streptococcus pyogenes* MGAS315, *Streptococcus pyogenes* MGAS8232, *Streptococcus pyogenes* SSI-1, *Streptomyces avermitilis*, *Streptomyces coelicolor*, *Tropheryma whipplei* TW08 27, and *Tropheryma whipplei* Twist. The amino acid sequences associated with the species-specific pentapeptides disclosed by Boekhorst et al., for the above microorganisms are summarized in Table 1, below.

The blocking groups, B, in the compound of Formula I are independently and at each occurrence —$CH_2OC(O)CH_3$ or a group of Formula II. In some embodiments, the group of Formula II is a 3-(2-acetoxy-4,6-dimethylphenyl)-3-methylbutanoyl ("trimethyl lock") group. The blocking groups render the latent fluorophore portion of the latent fluorescent tag non- or minimally fluorescent. However, in the living cellular environment, the blocking groups may be cleaved rendering a fluorescent cleavage product. In this regard, the blocking groups, which include ester linkages, may be cleaved in the cellular environment by esterase enzymes. A non-limiting illustration of this concept, based on trimethyl lock blocking groups and a rhodamine dye, is shown in FIG. 4. As previously set forth, when the latent fluorescent tag is contacted with the living cell, the sortase enzyme of the cell cleaves the polypeptide residue, covalently attaching the remainder of the latent fluorescent tag to the cell wall of the cell via the cleaved polypeptide residue. The trimethyl lock blocking groups of the latent fluorescent tag possess unfavorable steric interactions between neighboring methyl groups. Thus, enzymatic cleavage of the acetate groups of one or both of the trimethyl lock blocking groups results in the rapid expulsion of 4,4,5,7-tetramethylchroman-2-one with concomitant unmasking of the latent fluorophore. In this manner, the cell is covalently labeled with a fluorescent tag. Blocking groups of Formula II (including trimethyl lock groups) and —$CH_2OC(O)CH_3$ (i.e. acetoxymethyl ether blocking groups) generally display remarkable stability in aqueous solution yet rapidly release fluorescent compounds attached thereto upon exposure to esterase. Strategies employing trimethyl lock and acetoxymethyl ether blocking groups with fluorescent compounds, including fluorescein and rhodamine dyes, have been described by: Raines, R. et al., U.S. Pat. No. 7,534,902; Chandran, S. et al., J. Am. Chem. Soc. 2005, 127, 1652-1653; Lavis, L. et al., Chem. Sci., 2011, 2, 521-530; and Lavis, L. et al., ChemBioChem 2006, 7, 1151-1154; Mangold, S. et al., Org. Lett 2008, 10(14), 2997-3000.

The polypeptides of the latent fluorescent tags of the present technology may include, but are not limited to, any of the sortase recognition sequences embraced by Table 1. Thus, in some embodiments, the polypeptide, P, in the group of Formula III of the latent fluorescent tags of the present technology is a group of Formula IV:

$Xaa_1$-$Xaa_2$-$Xaa_3$-$Xaa_4$-$Xaa_5$ (SEQ ID NO: 1)     IV wherein each of $Xaa_1$, $Xaa_2$, $Xaa_3$, $Xaa_4$, and $Xaa_5$ is selected from the indicated amino acids in Table 1. For example, the polypeptide may be a pentapeptide with any of the following sequences: LPKTG (SEQ ID NO: 6), LPNTG (SEQ ID NO: 7), LPETG (SEQ ID NO: 2), LPQTG (SEQ ID NO: 8), LPATG (SEQ ID NO: 9), LPNTA (SEQ ID NO: 10), LAETG (SEQ ID NO: 11), or NPQTN (SEQ ID NO: 4). It will be understood by those of skill in the art that the peptide sequences represented by Formula IV are read from left to right, with the N-terminus on the left of each residue and the C-terminus on the right, and that each pair of adjacent residues are linked via a peptide bond between the C-terminus of one residue and the N-terminus of the adjacent residue.

In some embodiments of the present technology, the polypeptide, P, in the group of Formula III of the latent fluorescent tags of the present technology is selected from the group consisting of the formulae in Table 2, wherein each of $Xaa_1$, $Xaa_2$, $Xaa_3$, $Xaa_4$, and $Xaa_5$ are selected from the indicated amino acids in Table 1.

TABLE 2

| Formula | Sequence | SEQ ID NO: |
|---------|----------|------------|
| IVA | Leu-Pro-$Xaa_3$-Thr-$Xaa_5$ | 12 |
| IVB | Leu-Pro-$Xaa_3$-Thr-Gly | 13 |
| IVC | Leu-Pro-$Xaa_3$-$Xaa_4$-Gly | 14 |
| IVD | Leu-Pro-$Xaa_3$-Ala-Gly | 15 |
| IVE | Leu-Pro-$Xaa_3$-Thr-Ser | 16 |
| IVF | Leu-Pro-$Xaa_3$-Thr-Asn | 17 |
| IVG | Leu-Ala-$Xaa_3$-Thr-Gly | 18 |
| IVH | Leu-Ser-$Xaa_3$-Thr-Gly | 19 |
| IVI | Ile-Pro-$Xaa_3$-Thr-Gly | 20 |
| IVJ | Phe-Pro-$Xaa_3$-Thr-Gly | 21 |
| IVK | Leu-Pro-$Xaa_3$-Thr-Ala | 22 |

In some embodiments of the present technology, the polypeptide has Formula IVD and $Xaa_3$ is selected from any of A, E, H, K, L, N, Q, S, or T. In other embodiments, the polypeptide has Formula IVE and $Xaa_3$ is selected from any of D, K, N, Q, S, or T. In other embodiments, the polypeptide has Formula IVF and $Xaa_3$ is selected from any of K, M, N, Q, or T. In others, the polypeptide has Formula IVG and $Xaa_3$ is selected from any of A, D, E, F, H, K, L, N, R, S, or Y. In other embodiments, the polypeptide has Formula IVH and $Xaa_3$ is selected from any of F, N, or S. In other embodiments, the polypeptide has Formula IVI and $Xaa_3$ is selected from any of D, E, K, M, N, Q, or R. In other embodiments, the polypeptide has Formula IVJ and $Xaa_3$ is selected from any of K, Q, or S. In other embodiments, the polypeptide has Formula IVK and $Xaa_3$ is selected from any of D, E, K, or N.

In certain embodiments, the polypeptide of Formula IV has a sequence selected from AKKEK (SEQ ID NO: 23), FPKTG (SEQ ID NO: 24), FPQTG (SEQ ID NO: 25), FPSTG (SEQ ID NO: 26), GPDTA (SEQ ID NO: 27), IPALG (SEQ ID NO: 28), IPDTG (SEQ ID NO: 29), IPETG (SEQ ID NO: 30), IPKTG (SEQ ID NO: 31), IPMTG (SEQ ID NO: 32), IPNTG (SEQ ID NO: 33), IPQTG (SEQ ID NO: 34), IPRTG (SEQ ID NO: 35), IVKTG (SEQ ID NO: 36), LAATG (SEQ ID NO: 37), LADTG (SEQ ID NO: 38), LAETG (SEQ ID NO: 11), LAHTG (SEQ ID NO: 39), LAFTG (SEQ ID NO: 40), LAKTG (SEQ ID NO: 41), LALTG (SEQ ID NO: 42), LANTG (SEQ ID NO: 43), LARTG (SEQ ID NO: 44), LASTG (SEQ ID NO: 45), LAYTG (SEQ ID NO: 46), LAETP (SEQ ID NO: 47), LEKTN (SEQ ID NO: 48), LGATG (SEQ ID NO: 49), LGNTG (SEQ ID NO: 50), LLKTG (SEQ ID NO: 51), LPAAG (SEQ ID NO: 52), LPEAG (SEQ ID NO: 53), LPHAG (SEQ ID NO: 54), LPKAG (SEQ ID NO: 55), LPLAG (SEQ ID NO: 56), LPNAG (SEQ ID NO: 57), LPQAG (SEQ ID NO: 58), LPSAG (SEQ ID NO: 59), LPTAG (SEQ ID NO: 60), LPKAN (SEQ ID NO: 61), LPEKG (SEQ ID NO: 62), LPALG (SEQ ID NO: 63), LPQMN (SEQ ID NO: 64), LPDTA (SEQ ID NO: 65), LPETA (SEQ ID NO: 66), LPKTA (SEQ ID NO: 67), LPNTA (SEQ ID NO: 10), LPFSG (SEQ ID NO: 68), LPSSG (SEQ ID NO: 69), LPQTD (SEQ ID NO: 70), LPATG (SEQ ID NO: 9), LPDTG (SEQ ID NO: 71), LPETG (SEQ ID NO: 2), LPFTG (SEQ ID NO: 73), LPGTG (SEQ ID NO: 74), LPHTG (SEQ ID NO: 75), LPITG (SEQ ID NO: 76), LPKTG (SEQ ID NO: 6), LPLTG (SEQ ID NO: 77), LPMTG (SEQ ID NO: 78), LPNTG (SEQ ID NO: 7), LPQTG (SEQ ID NO: 8), LPRTG (SEQ ID NO: 79), LPSTG (SEQ ID NO: 80), LPTTG (SEQ ID NO: 81), LPVTG (SEQ ID NO: 82), LPYTG (SEQ ID NO: 83), LPKTN (SEQ ID NO: 84), LPMTN (SEQ ID NO: 85), LPNTN (SEQ ID NO: 86), LPQTN (SEQ ID NO: 87), LPTTN (SEQ ID NO: 88), LPDTS (SEQ ID NO: 89), LPKTS (SEQ ID NO: 90), LPNTS (SEQ ID NO: 91), LPQTS (SEQ ID NO: 92), LPSTS (SEQ ID NO: 93), LPETV (SEQ ID NO: 94), LPIVG (SEQ ID NO: 95), LPIYS (SEQ ID NO: 96), LSNTG (SEQ ID NO: 97), LSSTG (SEQ ID NO: 98), LSFTG (SEQ ID NO: 99), NAKTN (SEQ ID NO: 100), NAKTS (SEQ ID NO: 101), NKKSA (SEQ ID NO: 102), NPKTG (SEQ ID NO: 103), NPQTG (SEQ ID NO: 104), NPQTN (SEQ ID NO: 4), NPTKQ (SEQ ID NO: 105), NDTAV (SEQ ID NO: 106), NPKSS (SEQ ID NO: 107), NSKTA (SEQ ID NO: 108), PETGE (SEQ ID NO: 109), PKTGE (SEQ ID NO: 110), VPTGV (SEQ ID NO: 111), VANTG (SEQ ID NO: 112), VPDTG (SEQ ID NO: 113), VPPTG (SEQ ID NO: 114), YPKTG (SEQ ID NO: 115), or YPRTG (SEQ ID NO: 116).

Nelson, et al., (ACS Chemical Biology 2010, 5(12), 1147-115) have shown that polypeptides, such as those disclosed by Boekhorst et al., can be directly coupled to small molecules for covalent incorporation into cell walls, with incorporation levels of up to 6500 polypeptides per cell, of which about 1000 fluorescent molecules per cell were readily detectable. However, in contrast to the findings of Nelson et al., in which the fluorescent molecules are always activated whether or not bound to the cell, the present technology provides vastly improved signal to background since only tagged and living cells fluoresce.

The polypeptide portion of the latent fluorescent tags of the present technology are readily synthesized using standard peptide coupling techniques and reagents well known in the art, such as those described in *Peptide Synthesis Protocols*, Pennington, M. W., Dunn, B. M. (Eds.) Humana Press, Inc., New Jersey, 1994 and in Bodansky, M. and A. Bodansky, A. *The Practice of Peptide Synthesis*, Springer-Verlag, New York 1984. The polypeptides may be synthesized in solution phase, or may be synthesized using solid phase resins and/or supports (e.g., rink resins, amide resins, polystyrene resins, and the like). The synthesis may be automated. As further described below, the linker portion of the present latent fluorescent tags may also include amino acids. Thus, a polypeptide-linker conjugate (i.e., the polypeptide covalently attached to the linker) may be readily prepared directly using peptide synthesis techniques.

The polypeptide of the latent fluorescent tags of the present technology is attached to the latent fluorophore by a linker. The linker is attached to the N-terminus of the polypeptide. In general, any linker may be used, providing such linker is compatible with the cellular environment. For example, the linker should not substantially degrade in the cellular environment. The linker should be of sufficient flexibility and length to provide the physical freedom for the latent fluorophore (or activated form thereof) to extend to either side of the cell wall. The linker should also be of sufficient hydrophobic or hydrophobic/hydrophilic such that the linker may readily traverse the hydrophobic cell wall membrane. While not wishing to be bound by theory, it is believed that although active endocytosis (active cellular uptake) of the latent fluorophore may occur, entrance of the latent fluorophore into the cell may occur primarily by passive diffusion, especially of the anchored latent fluorophore. For example, once the sortase enzyme cleaves the polypeptide and covalently attaches the remainder of the tag to the cell via the cleaved polypeptide residue, the extent of movement of the latent fluorophore is provided by the length of the linker. Thus, possible locations of the linked latent fluorophore include outside of the cell, in the cell wall, and inside the cell. Once inside the cell, the latent fluorophore may be activated as described herein.

The linker may be an amino acid linker having 1, 2, 3, 4, 5, 6, 7, 8, 9, 10, 11, 12, 13, 14, 15, 16, 17, 18, 19, or 20 amino acid residues or any range of amino acid residues between and including such values. For example the linker may include 1 to about 20, 1 to about 15, 1 to about 10, or 1 to about 5, amino acid residues. The amino acid linker may include hydrophobic amino acids. The term "hydrophobic amino acid" refers an amino acid which is more hydrophobic than Gly at a given pH. The relative hydrophobicity of an amino acid in comparison to Gly may be obtained from its hydrophobicity index, where the most hydrophobic natural amino acid is given a value of 100 relative to Gly which is considered neutral (i.e., a value of zero). For example, at pH 2, reported hydrophobicity index values for certain hydrophobic amino acids are: Leu, 100; Ile, 100; Phe, 92; Trp, 84; Val, 79; Met, 74; Cys, 52; Tyr, 49; Ala, 47. Similarly, hydrophilic amino acids are more hydrophilic than Gly at a given pH: Arg, −26; Lys, −37; Asn, −41; His, −42; Pro, −46. Neutral amino acid residues may be slightly more hydrophilic or hydrophobic than Gly. Thus at pH 2, such amino acids include: Thr, 13; Glu, 8; Gly, 0; Ser, −7; Gln, −18; Asp, −18; and hydrophilic amino acids are: (see Sereda et al., "Reversed-phase chromatography of synthetic amphipathic alpha-helical peptides as a model for ligand/receptor interactions. Effect of changing hydrophobic environment on the relative hydrophilicity/hydrophobicity of amino acid side-chains." J. Chrom. 1994, 676, 139-153). At pH 7, reported hydrophobicity index values for hydrophobic amino acids are: Phe, 100; Ile, 99; Trp, 97; Leu, 97; Val, 76; Met, 74; Tyr, 63; Cys, 49; Ala, 41; neutral amino acid residues: Thr, 13; His, 8; Gly, 0; Ser, −5; Gln, −10; Arg, −14; and hydrophilic amino acids are: Lys, −23; Asn, −28; Glu, −31; Asp, −55 (see Monera et al., "Relationship of sidechain hydrophobicity and α-helical propensity on the stability of the single-stranded amphipathic α-helix." J. Pep. Sci., 1995, 1, 319-329). In some embodiments, the amino acid linker consists of one or more of Lys (i.e., a polylysine linker) or consists of one or more Gly (i.e., a polyglycine linker).

The polypeptide of the latent fluorescent tags of the present technology is attached to the latent fluorophore by a linker. The linker is attached to the N-terminus of the polypeptide. In general, any linker may be used, providing such linker is compatible with the cellular environment. For example, the linker should not substantially degrade in the cellular environment. The linker should be of sufficient flexibility and length to provide the physical freedom for the latent fluorophore (or activated form thereof) to extend to either side of the cell wall. The linker should also be of sufficient hydrophobic or hydrophobic/hydrophilic such that the linker may readily traverse the hydrophobic cell wall membrane. While not wishing to be bound by theory, it is believed that although active endocytosis (active cellular uptake) of the latent fluorophore may occur, entrance of the latent fluorophore into the cell may occur primarily by passive diffusion, especially of the anchored latent fluorophore. For example, once the sortase enzyme cleaves the polypeptide and covalently attaches the remainder of the tag to the cell via the cleaved polypeptide residue, the extent of movement of the latent fluorophore is provided by the length of the linker. Thus, possible locations of the linked latent fluorophore include outside of the cell, in the cell wall, and inside the cell. Once inside the cell, the latent fluorophore may be activated as described herein.

The linker may be a substituted or unsubstituted C1 to C30 alkylene group. Such a linker may also include one or more functional groups such as carbonyls, esters, amides, ethers, amines, imines, urethanes, imides, sulfoxides, sulfones, sulfonamides, and disulfides, and the like. Such functional groups may arise from reaction of the linker with the polypeptide and/or the linker with the latent fluorophore (or functional groups on the latent fluorophore). Additionally or alternatively, such functional groups may be present within the linker itself. The linker may be an amino-substituted alkanoic acid which includes a carboxylate group and an amino group. Examples of such linkers include, but are not limited to, 4-aminobutanoic acid, 5-aminopentanoic acid, 6-aminohexanoic acid, 7-aminoheptanoic acid, 8-aminooctanoic acid, a higher aminoalkanoic acid (e.g., C9 to C30), or an N-protected derivative of any of the foregoing. Such amino-substituted alkanoic acids and N-protected derivatives are commercially available (e.g., Sigma-Aldrich, St. Louis, Mo.) or are readily synthesized using techniques known in the art. Examples of suitable nitrogen protecting groups include, but are not limited to tert-butoxycarbonyl (Boc) and 9-fluorenyl-methyloxycarbonyl (Fmoc) groups. An amino-substituted alkanoic acid linker (or protected derivatives thereof) may be attached via its C-terminus to the N-terminus of the polypeptide. The N-terminus of the amino-substituted alkanoic acid may be attached to the latent fluorophore directly, or through a reactive group on the latent fluorophore (e.g., via an amide bond formed from by reaction of the N-terminus of the linker with a carboxylate-functionalized latent fluorophore. In some such embodiments, the linker is a substituted or unsubstituted C1 to C10 alkylene linker.

The linker L may be a substituted or unsubstituted C1 to C30 heteroalkylene linker. The heteroatoms (e.g., one or more of N, O, S) of the heteroalkylene linker may be integral to the linker and/or located at the either or both termini of the linker. Like C1 to C30 alkylene linkers, heteroalkyene linkers may also include one or more functional groups such as carbonyls, esters, amides, ethers, amines, imines, urethanes, imides, sulfoxides, sulfones, sulfonamides, disulfides, and the like.

Figure 3:
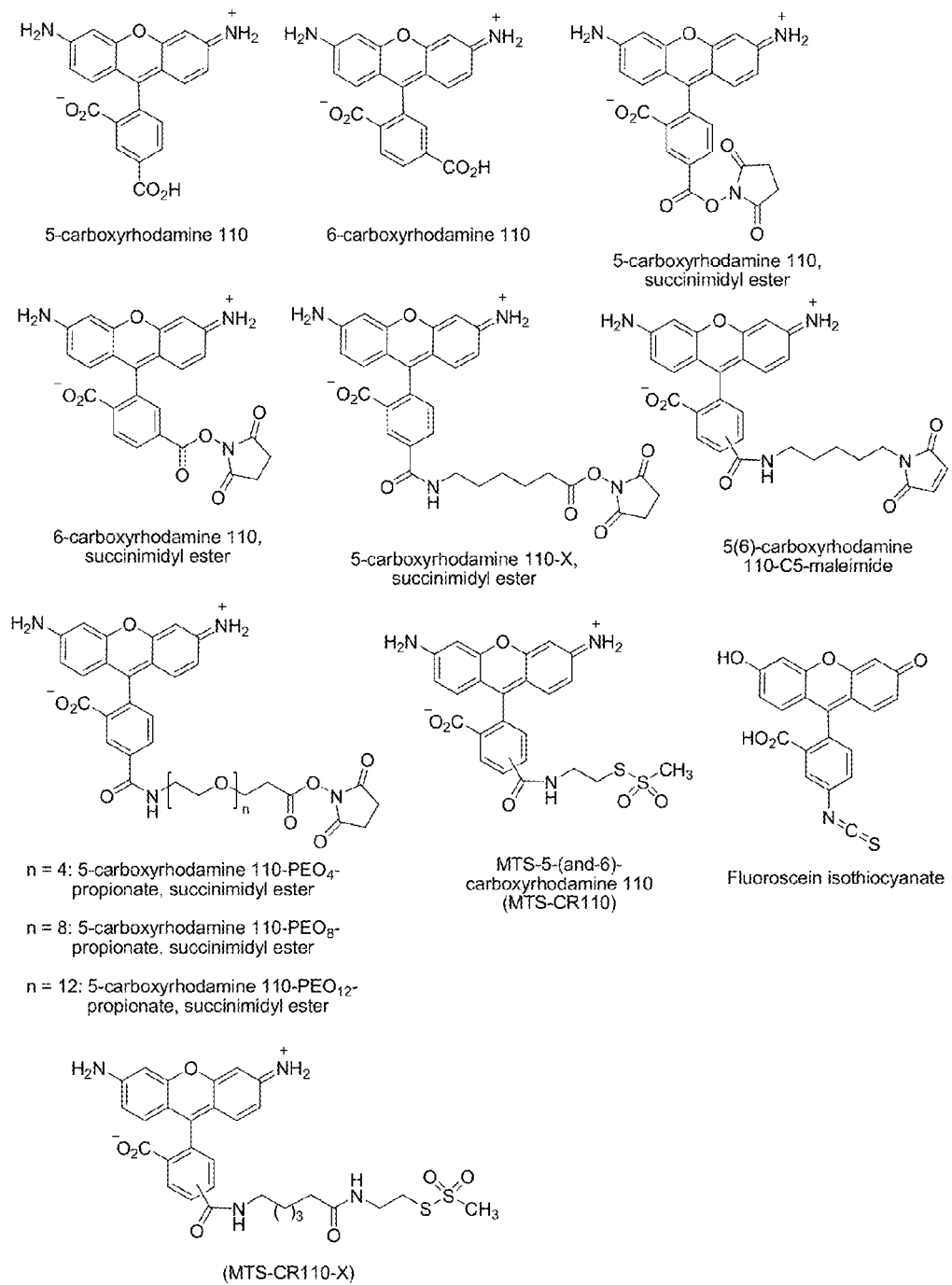
FIG. 3 shows examples of commercially available rhodamine and fluorescein dyes which may be used to prepare latent fluorescent tags, according to some embodiments.

In some embodiments of the compounds of Formula I, the linker is a substituted or unsubstituted poly(oxyalkylene) wherein the alkylene is a C2 to C10 alkylene. Examples of poly(oxyalkylene) linker include poly(oxyethylene) and poly (oxypropylene). In some embodiments, the linker is poly (oxyethylene). As shown in FIG. 3, certain rhodamine dyes which include poly(oxyalkylene) linkers are commercially available, from which compounds of Formula I or Formula IA may be prepared.

As will be appreciated by those of skill in the art, any of the linkers described herein may be modified as to allow for the attachment of 2, 3, 4, or more latent fluorophores. For example, two latent fluorophores may be attached to an amino acid linker which includes a terminal Arg residue. In this regard, a first latent fluorophore may be attached to the N-terminus of the Arg residue and a second latent fluorophore (which may be the same or different) may be attached to the guanidine side chain of the Arg residue. To facilitate attachment of the first and second latent fluorophores to such an Arg-containing linker, the first and second latent fluorophores may include any of the reactive groups previously described, such as carboxylic acid groups (e.g., attachment of the first latent fluorophore to the Arg residue via an amide group and attachment of the second latent fluorophore to the same Arg residue via a —C(O)NHC(═NH)NH— group). Of course, a linker which includes multiple Arg residues may be modified to include additional latent fluorophore groups.

In some embodiments the compound of Formula I is a compound of Formula IA:

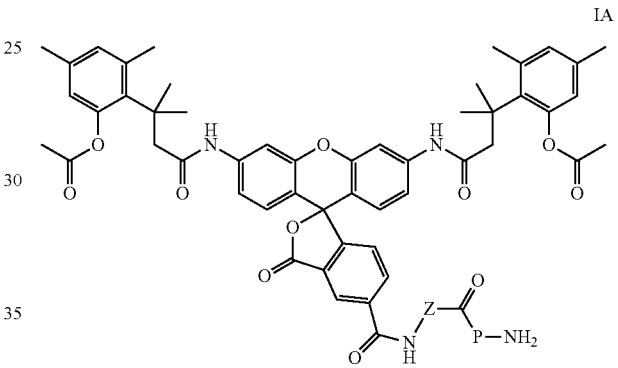

IA wherein Z is selected from the group consisting of substituted or unsubstituted C1 to C10 alkylene and substituted or unsubstituted C1 to C10 heteroalkylene, or when taken together with the NH and C═O moieties bonded thereto is an amino acid linker comprising from 1 to about 20 amino acids.

Figure 5:
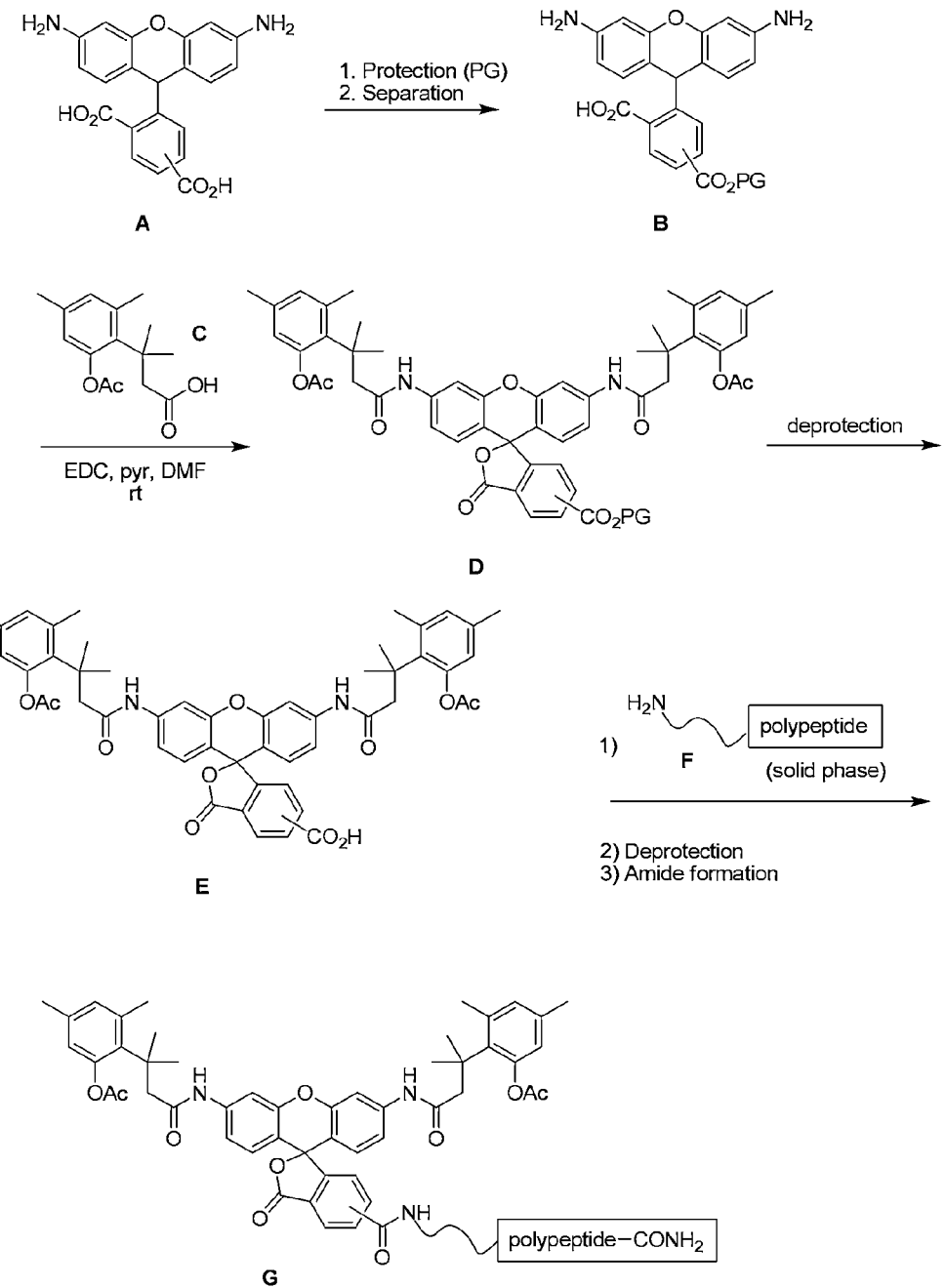
FIG. 5 is a schematic illustration of the synthesis of latent fluorescent tags of the present technology from carboxylate-functionalized rhodamine dyes, according to some embodiments.

Compounds of Formulas I or IA may be prepared using synthetic techniques well known in the art. For example, as shown in FIG. 5, carboxylate-functionalized rhodamine dye A (e.g., 5-, 6-, or 5/6-carboxyrhodamine 110, commercially available from Biotium (Hayward, Calif.)) may be selectively protected as an ester (e.g., methyl, t-butyl, benzyl, or the like) group using techniques well known in the art to provide compound B. An extensive list of protecting groups for carboxylate and other functional groups may be found in Protective Groups in Organic Synthesis, Greene, T. W.; Wuts, P. G. M., John Wiley & Sons, New York, N.Y. (3rd Edition, 1999), which can be added or removed using the procedures and reagents set forth therein, and which is hereby incorporated by reference in its entirety and for all purposes as if fully set forth herein. The protecting group may be a sterically bulky group such as t-butyl group. In this regard, steric interactions will favor the selective protection of the less hindered carboxylate group of compound A. Where mono- and di-protected carboxylates are formed, the desired mono-protected carboxylate (i.e., compound A) may separated by common purification techniques, including but not limited to crystallization, sublimation, or chromatography. The undesired di-protected carboxylate (not shown) may be hydrolyzed back to the starting material and reused. Treatment of B with trimethyl lock reagent C (prepared according the methods described by Amsberry, K. et al.; Pharm. Res. 1991, 8, 455-461 and Nicolaou, M. et al., J. Org. Chem. 1996, 61, 8636-8641, each of which are hereby incorporated by reference in their entireties and for all purposes as if fully set forth herein) in the presence of a coupling reagent such as 1-ethyl-3-(3-dimethylaminopropyl)carbodiimide (EDC) provides compound D. Deprotection of compound D with reagents as described in Protective Groups in Organic Synthesis provides compound E. For example, if the protecting group is a sterically bulky group such as t-butyl, as mentioned above, example deprotection reactions may include, but are not limited to: contact with potassium t-butoxide in water; contact with aqueous sodium hydroxide in the presence of dimethylformamide; contact with magnesium iodide in toluene; or the like. In the event that deprotection reaction conditions convert some of the lactone form of compound E to a ring-opened dicarboxylate form, either milder deprotection conditions may be selected to avoid ring-opening of the lactone form of compound E, or mild oxidation conditions may be employed on the ring-opened dicarboxylate form of E to convert back to the lactone form. Coupling of compound E to solid-phase supported polypeptide-linker conjugate F in the presence of a peptide coupling reagent such as N,N'-dicyclohexylcarbodiimide or N,N'-diisopropylcarbodiimide, followed by deprotection with a solid phase cleavage reagent such as trifluoroacetic acid, followed by terminal amide formation provides latent fluorescent tag G. If a suitable solid phase is employed, such as paramethylbenzhydrylamine (pMBHA) resin, cleavage yields a corresponding C-terminal amide without the need for a separate step to form a C-terminal amide. Suitable resins are commercially available, for example, 4-(2',4'-dimethoxyphenyl-Fmoc-aminomethyl-phenoxy-acetamido-norleucylaminomethyl resin and 4-(2',4'-Dimethoxyphenyl-Fmoc-aminomethyl-phenoxy-acetamido-norleucyl-MBHA resin (Glycopep Chemicals Inc. Chicago Ill.). The solid-phase supported polypeptide-linker conjugate F (for example, Lys-Lys-Lys-Lys-Lys-Leu-Pro-Glu-Thr-Gly-solid phase (SEQ ID NO: 117) or $H_2NCH_2(CH_2)_6C(O)$-Leu-Pro-Glu-Thr-Gly-solid phase (SEQ ID NO: 2), both of which includes an LPETG (SEQ ID NO: 2) sortase recognition sequence for S. Aureus) may be prepared by standard peptide coupling techniques known in the art.

Figure 6:
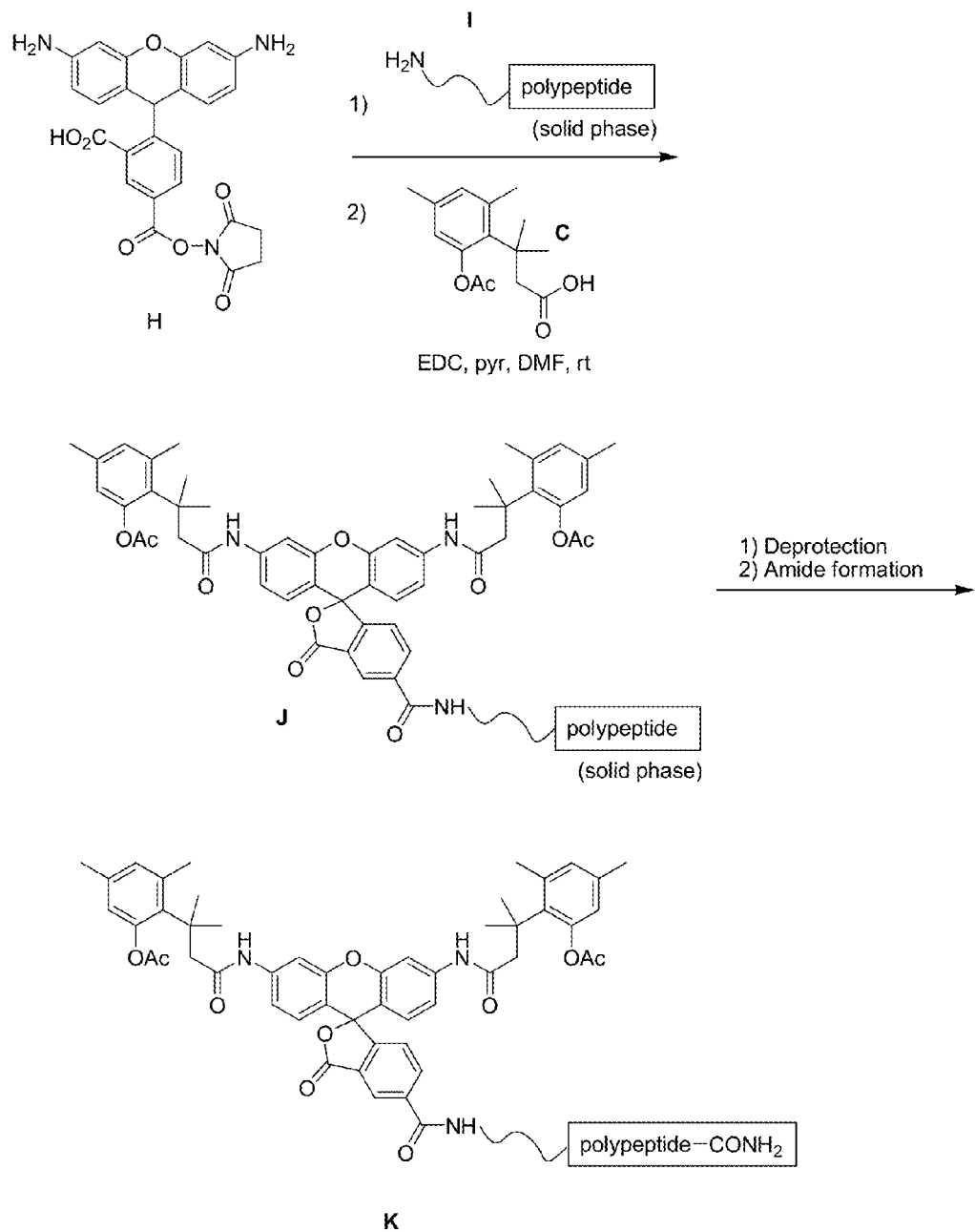
FIG. 6 is a schematic illustration of the fluorescent labeling of a live cell with a latent fluorescent tag including a rhodamine dye portion and trimethyl lock blocking groups, according to one embodiment.

Compounds of Formulas I or IA may also be prepared by reaction of amine-reactive dyes directly with a terminal amine group of a preformed solid-phase supported polypeptide-linker conjugate. For example, as shown in FIG. 6, a commercially available amine-reactive N-hydroxysuccinimide-functionalized dye H is first coupled to solid-phase supported polypeptide-linker conjugate I (for example, Gly-Gly-Gly-Gly-Gly-Gly-Gly-Gly-Leu-Pro-Glu-Thr-Gly-solid phase (SEQ ID NO: 118) or $H_2NCH_2(CH_2)_6C(O)$-Leu-Pro-Glu-Thr-Gly-solid phase (SEQ ID NO: 2), both of which includes an LPETG (SEQ ID NO: 2) sortase recognition sequence for S. Aureus) and the amine groups are subsequently masked with trimethyl lock reagent C in the presence of EDC to provide solid phase-supported compound J. Cleavage of compound J from a suitable pMBHA resin as described above provides C-terminal amino latent fluorescent tag K.

Figure 7:
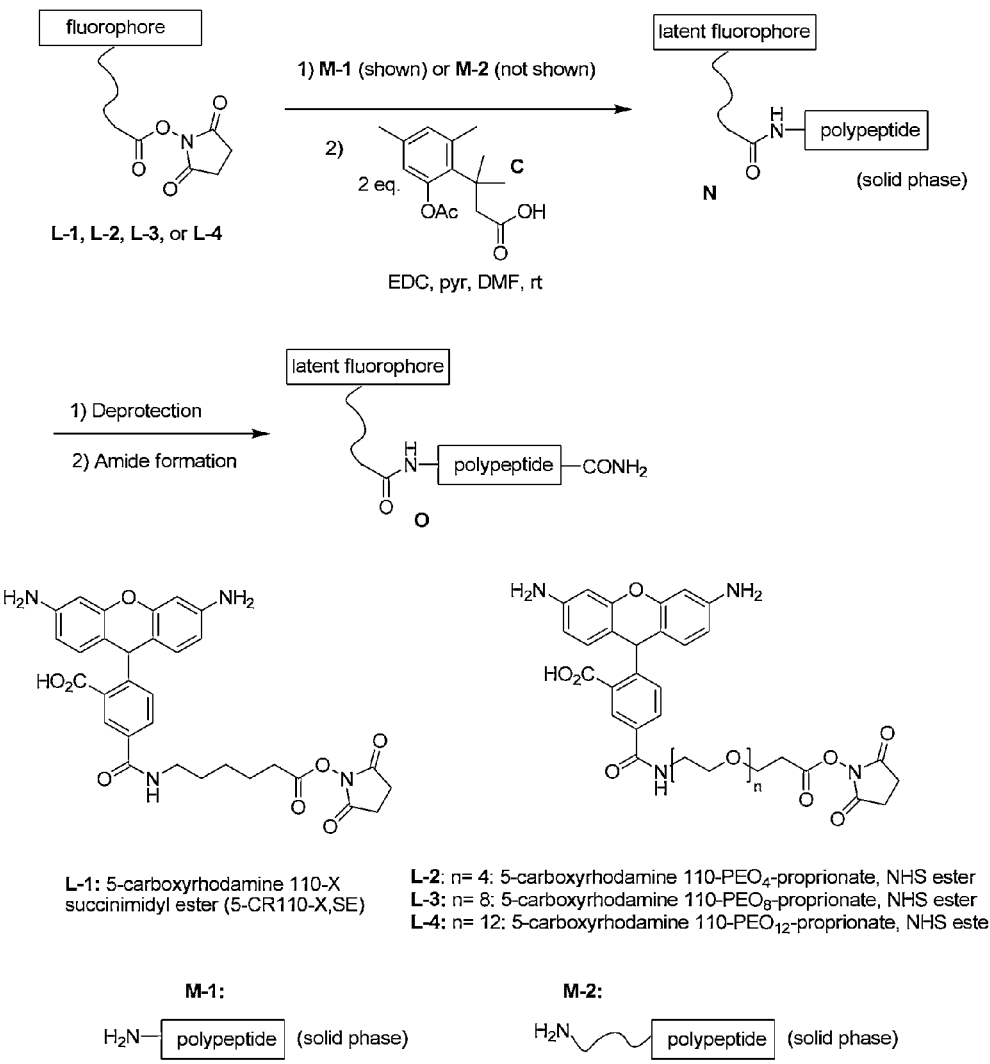
FIG. 7 is a schematic illustration of the synthesis of latent fluorescent tags of the present technology from rhodamine dyes including a linker or portion a portion of a linker, according to some embodiments.

In another manner, the compounds of Formulas I or IA may be prepared from rhodamine or fluorescein dyes which include linkers, or portions of linkers. For example, as shown in FIG. 7, any of the commercially amine-reactive dyes L-1, L-2, L-3, or L-4 may be coupled to the free amine of solid-phase supported polypeptide M-1 or solid-phase supported polypeptide-linker conjugate M-2 (for example, Gly-Lys-Gly-Lys-Gly-Lys-Leu-Pro-Glu-Thr-Gly-solid phase (SEQ ID NO: 119), $H_2NCH_2(CH_2)_6C(O)$-Leu-Pro-Glu-Thr-Gly-solid phase (SEQ ID NO: 2), or Leu-Pro-Glu-Thr-Gly-solid phase (SEQ ID NO: 2), all of which include an LPETG (SEQ ID NO: 2) sortase recognition sequence for S. Aureus). Thus, coupling of any of amine-reactive dyes L-1, L-2, L-3, or L-4 with polypeptide M-1 followed by masking of the arylamine groups with trimethyl lock reagent C in the presence of EDC provides solid phase-supported compound N. Cleavage of compound N from a suitable pMBHA resin as described above provides C-terminal amino latent fluorescent tag O.

Figure 8:
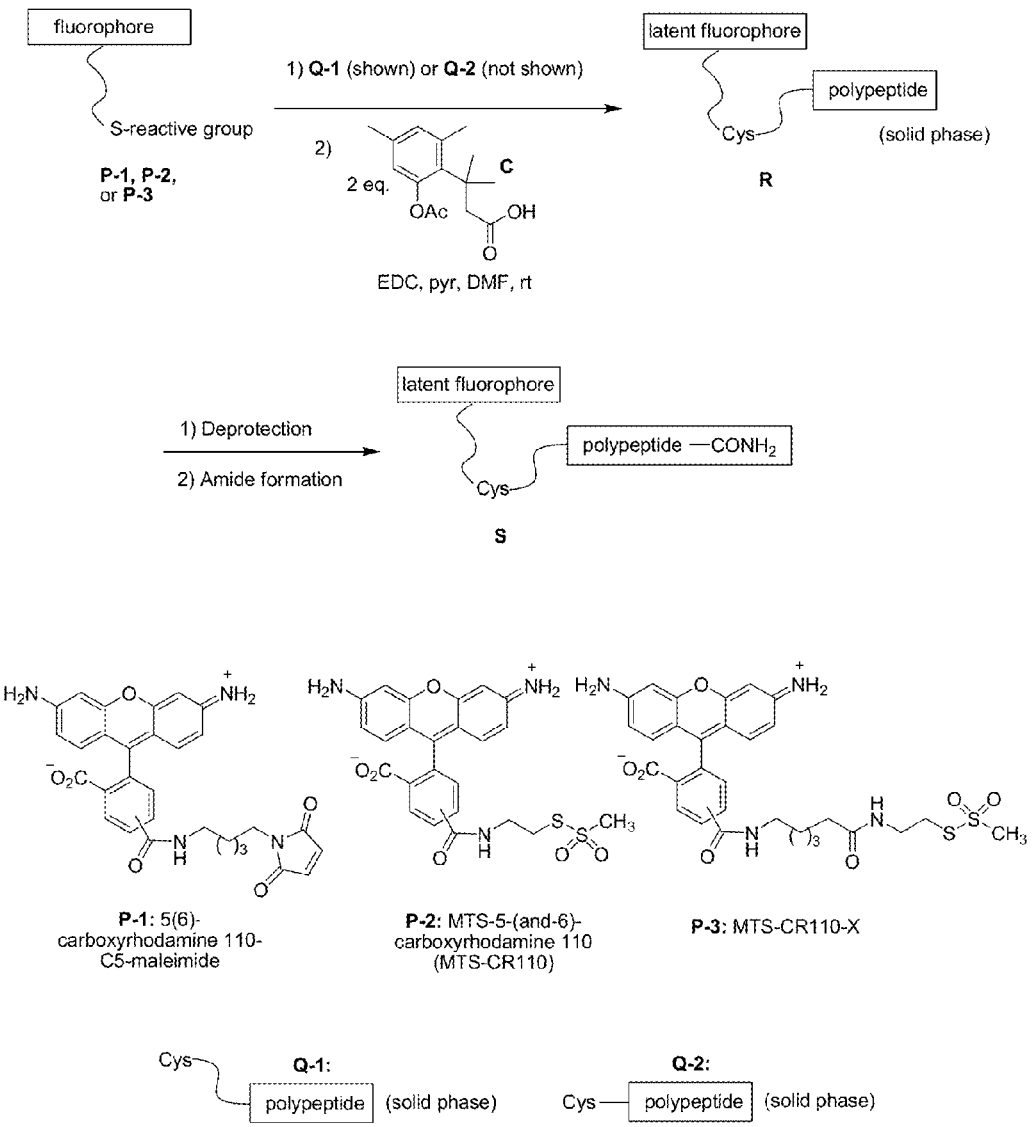
FIG. 8 is a schematic illustration of the synthesis of latent fluorescent tags of the present technology from rhodamine dyes including sulfur-reactive groups, according to some embodiments.

Compounds of Formulas I or IA may also be prepared from thiol-reactive rhodamine or fluorescein dyes. For example, as shown in FIG. 8, any of the commercially available dyes P-1, P-2, or P-3 which include thiol reactive groups (i.e., maleimide and methanesulfonothionate groups) may be coupled to a solid-phase supported polypeptide-linker conjugate Q-1 which includes a thiol group at the linker terminus (e.g., in the form of a Cys group) or may be coupled to a solid-phase supported polypeptide terminated with a Cys residue at the N-terminus of the polypeptide (Q-2). In this manner, a solid-supported polypeptide-linker conjugate or polypeptide such as Cys-Gly-Gly-Gly-Gly-Gly-Gly-Leu-Pro-Glu-Thr-Gly-solid phase (SEQ ID NO: 120), $HSCH_2(CH_2)_{10}C(O)$-Leu-Pro-Glu-Thr-Gly-solid phase (SEQ ID NO: 2), or Cys-Leu-Pro-Glu-Thr-Gly-solid phase (SEQ ID NO: 121) (each of which include an LPETG (SEQ ID NO: 2) sortase recognition sequence for S. Aureus) may be coupled to the thiol reactive dye. For example, reaction of P-1, P-2, or P-3 with Cys-containing Q-1 provides followed by masking of the arylamine groups with trimethyl lock reagent C provides solid-phase supported R. Deprotection and amidation in the manner previously described provides latent fluorescent tag S.

According to another aspect, the present technology provides a method of labeling a living cell, the method comprising contacting at least one living cell with a compound of Formulas I or IA as described herein. In this regard, cells may be fluorescently labeled for a variety of purposes, including cell counting, cell imaging, and cell identification. Typically, the living cell produces a sortase enzyme, or a sortase enzyme is otherwise present in the living cell. In some embodiments, the living cell is that of a Gram-positive bacterium such as one or more species of *Clostridium, Enterococcus, Staphylococcus, Streptococcus, Actinobacter, Bacillus, Listeria,* or *Corynebacterium*. As described herein, the compound of Formula I or IA may be cleaved at the polypeptide by a sortase enzyme, and the remainder of the compound of Formula I or IA, with or without blocking groups is covalently bound to the cell, such as to the cell wall of the cell. Thus, in another embodiment, the compound of Formula I or IA or a metabolite of either thereof is bound to the living cell after the contacting step.

The detection of fluorescence from a cell which has been contacted with the compound of Formula I or IA may be achieved by a variety of methods known in the art, such as fluorescence microscopy techniques. Briefly, a cell which has been contacted with the compound of Formula I or IA (i.e., and thus includes a covalently bound fluorophore) is illuminated with light of a wavelength which causes the fluorescence in the sample. The light emitted by fluorescence, which is at a different, longer, wavelength than the illumination, is then detected through a microscope objective. Typically, two filters are normally used in this technique; an illumination (or excitation) filter which ensures the illumination is near monochromatic and at the correct wavelength, and a second emission (or detection) filter which ensures none of the excitation light source reaches the detector.

As will be appreciated from the description provided herein, since the present latent fluorescent tags may be adapted for the fluorescent labeling of a given bacterial species, it is thus possible to detect different fluorescence signals from a mixture of bacterial species. For example, food may be sampled, cultured, and contacted with a mixture of two compounds of Formula I (or Formula IA). A first compound of Formula I (or Formula IA) could be adapted as to selectively label S. Aureus and fluoresce at green wavelength and A second compound of Formula I (or Formula IA) could be adapted to selectively label L. monocytogenes and fluoresce at a red length. In this manner, the presence or absence of the pathogens S. Aureus and/or L. monocytogenes in the food may quickly be determined simultaneously by fluorescence microscopy (and further quantified if so desired).

The present technology, thus generally described, will be understood more readily by reference to the following Examples, which is provided by way of illustration and is not intended to be limiting of the present technology.

EXAMPLES

Example 1

Preparation of a Latent Fluorescent Tag

Figure 9:
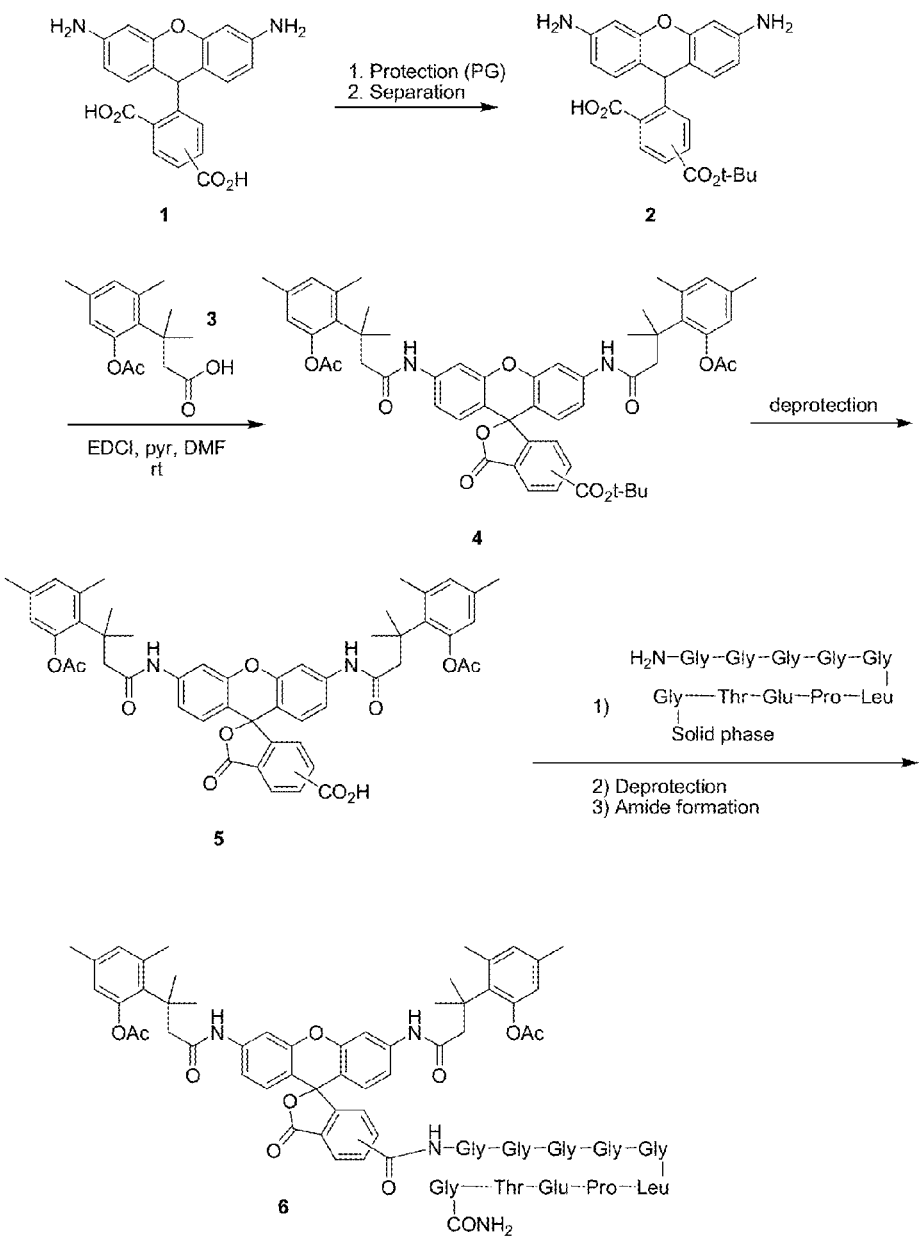
FIG. 9 is a schematic illustration of the synthesis of the latent fluorescent tag described in Example 1.

The preparation of compound 6, illustrated in FIG. 9, is as follows. In 10 mL of anhydrous tetrahydrofuran is dissolved 0.2 mmol of compound 1 as 5-carboxyrhodamine 110 (Biotium, Hayward, Calif.). This is combined with 0.4 mmol of dicyclohexyl carbodiimide, excess t-butyl alcohol, and a catalytic amount of dimethylamino pyridine. The mixture is stirred overnight and the product 5-t-butyl carboxy rhodamine 110, corresponding to structure 2, is separated by column chromatography. Unprotected or deprotected 5-carboxy rhodamine 110 is recovered and recycled. Next, 0.1 mmol 5-t-butyl carboxy rhodamine 110, 0.21 mmol of o-hydroxy cinnamic acid trimethyl lock reagent 3 (prepared according the methods described by Amsberry, K. et al., *Pharm. Res.* 1991, 8, 455-461 and Nicolaou, M. et al., *J. Org. Chem.* 1996, 61, 8636-8641) and 0.21 mmol ethylene carbodiimide with catalytic pyridine in dimethyl formamide provides 5-t-butyl carboxy compound 4. Compound 4 is dissolved in tetrahydrofuran and contacted with an excess of potassium t-butoxide in water to provide deprotected 5-carboxy lactone compound 5. Separately, standard peptide synthesis techniques are employed starting with a 4-(2',4'-dimethoxyphenyl-Fmoc-aminomethyl-phenoxy-acetamido-norleucylaminomethyl resin resin to result in a solid phase peptide of sequence $NH_2$-Gly-Gly-Gly-Gly-Gly-Leu-Pro-Glu-Thr-Gly-resin (SEQ ID NO: 122). Compound 5 is combined with a slight molar excess of a peptide coupling reagent such as N,N'-dicyclohexylcarbodiimide and contacted to the NH2-Gly-Gly-Gly-Gly-Gly-Leu-Pro-Glu-Thr-Gly-resin (SEQ ID NO: 122). Deprotection is accomplished using trifluoroacetic acid in water to form tag compound 6 directly from the resin as a C-terminal amino labeled peptide.

Example 2

Labeling of S. Aureus and Detection of Fluorescence

A test sample of media suspected of contamination with S. Aureus is contacted with an aqueous tag solution of about 0.001 M of structure G. The tag of structure G is configured to include an S. Aureus specific pentapeptide tage sequence LPETG (SEQ ID NO: 2). The combined test sample and tag solution are agitated and allowed to incubate for a period of time, and monitored via fluorescence spectrometry at the absorption and emission maxima characteristic of the fluorophore. As the S. Aureus cells incorporate the tag and convert the latent fluorophore to an active fluorophore, the mixture increases in fluoroescence. Live labeled S. Aureus in the sample may be imaged using fluorescence microscopy, since the activated fluorophores are covalently attached to the S. Aureus.

EQUIVALENTS

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

A test sample of media suspected of contamination with S. Aureus is contacted with an aqueous tag solution of about 0.001 M of structure G. The tag of structure G is configured to include an S. Aureus specific pentapeptide tag sequence LPETG (SEQ ID NO: 2). The combined test sample and tag solution are agitated and allowed to incubate for a period of time, and monitored via fluorescence spectrometry at the absorption and emission maxima characteristic of the fluorophore. As the S. Aureus cells incorporate the tag and convert the latent fluorophore to an active fluorophore, the mixture increases in fluorescence. Live labeled S. Aureus in the sample may be imaged using fluorescence microscopy, since the activated fluorophores are covalently attached to the S. Aureus.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

What is claimed is:

1. A compound of Formula I:

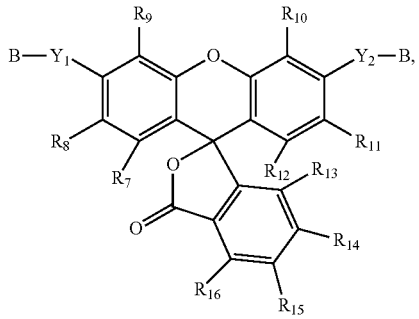

wherein:

B at each occurrence is independently —CH$_2$OC(O)CH$_3$ or a group of Formula II:

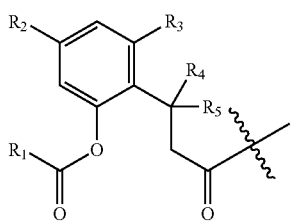

Y$_1$ and Y$_2$ are independently O or NR$_6$;

R$_1$, R$_2$, R$_3$, R$_4$, and R$_5$ at each occurrence are independently substituted or unsubstituted C1 to C8 alkyl;

R$_6$ at each occurrence is independently H or substituted or unsubstituted C1 to C8 alkyl;

R$_7$, R$_8$, R$_9$, R$_{10}$, R$_{11}$, R$_{12}$, R$_{13}$, R$_{14}$, R$_{15}$, R$_{16}$ are independently H, substituted or unsubstituted C1 to C8 alkyl, substituted or unsubstituted C6 to C14 aryl, substituted or unsubstituted C1 to C8 alkoxy, substituted or unsubstituted C6 to C14 aryloxy, hydroxy, halo, nitro, nitrile, amino, amido, imido, urea, amidine, guanidine, enamine, urethane, oxime, hydroxylamine, carboxyl, ester, oxo, thiol, sulfide, sulfoxide, sulfone, sulfonyl, sulfonate, sulfonamide, hydrazine, hydrazide, hydrazone, azide, cyanate, isocyanate, thiocyanate, or isothiocyanate; and one of R$_{13}$, R$_{14}$, R$_{15}$ or R$_{16}$ is a group of Formula III:

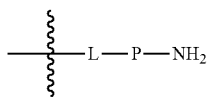

wherein:

L is a linker selected from the group consisting of substituted or unsubstituted C1 to C30 alkylene and substituted or unsubstituted C1 to C30 heteroalkylene, or is an amino acid linker comprising from 1 to about 20 amino acids; and P is a polypeptide comprising a C-terminus and an N-terminus, wherein the C-terminus of the polypeptide is bonded to the NH$_2$ moiety, and wherein P is cleavable by a sortase enzyme.

2. The compound of claim 1, wherein each B is a group of Formula II.

3. The compound of claim 2, wherein R$_1$ is methyl.

4. The compound of claim 2, wherein R$_2$, R$_3$, R$_4$, and R$_5$ are each methyl.

5. The compound of claim 1, wherein Y$_1$ is NH and Y$_2$ is NH.

6. The compound of claim 1, wherein R$_7$, R$_8$, R$_9$, R$_{10}$, R$_{11}$, R$_{12}$, R$_{13}$, R$_{14}$, and R$_{16}$ are each H.

7. The compound of claim 1, wherein each B is a group of Formula II, R$_1$, R$_2$, R$_3$, R$_4$, and R$_5$ are each methyl; R$_7$, R$_8$, R$_9$, R$_{10}$, R$_{11}$, R$_{12}$, R$_{13}$, R$_{14}$, and R$_{16}$ are each H; Y$_1$ is NH; and Y$_2$ is NH.

8. The compound of claim 1, wherein the amino acid linker comprises hydrophobic amino acids.

9. The compound of claim 1, wherein the amino acid linker consists of one or more Lys or consists of one or more Gly.

10. The compound of claim 1, wherein the linker is a substituted or unsubstituted C1 to C10 alkylene.

11. The compound of claim 1, wherein the linker comprises 4-aminobutanoic acid, 5-aminopentanoic acid, 6-aminohexanoic acid, 7-aminoheptanoic acid, 8-aminooctanoic acid, or an N-protected derivative of any of the foregoing.

12. The compound of claim 1, wherein the linker is a substituted or unsubstituted poly(oxyalkylene) wherein the alkylene is a C2 to C10 alkylene.

13. The compound of claim 1, wherein the linker is poly (oxyethylene).

14. The compound of claim 1, wherein the linker comprises one or more functional groups selected from the group consisting of carbonyls, esters, amides, ethers, amines, imines, urethanes, imides, sulfoxides, sulfones, sulfonamides, and disulfides.

15. The compound of claim 1, wherein the linker is covalently attached to both P and the compound of Formula I through amide functional groups.

16. The compound of claim 1, wherein the linker is covalently attached to P through a disulfide bond.

17. The compound of claim 1, wherein P is a pentapeptide or a hexapeptide.

18. The compound of claim 1, wherein P is a group of Formula IV:

$$Xaa_1\text{-}Xaa_2\text{-}Xaa_3\text{-}Xaa_4\text{-}Xaa_5 \text{ (SEQ ID NO: 1)} \qquad \text{IV}$$

wherein:

Xaa$_1$ is an amino acid selected from the group consisting of L, N, A, I, G, V, P, F, and Y;

Xaa$_2$ is an amino acid selected from the group consisting of P, S, E, G, K, A, D, V, and L;

Xaa$_3$ is an amino acid selected from the group consisting of K, A, N, Q, E, T, P, S, H, D, I, R, V, M, F, L, Y, and G;

Xaa$_4$ is an amino acid selected from the group consisting of T, A, K, G, S, Y, E, M, V, and L; and Xaa$_5$ is an amino acid selected from the group consisting of G, A, S, D, N, V, Q, E, K and P.

19. The compound of claim 1, having the Formula IA:
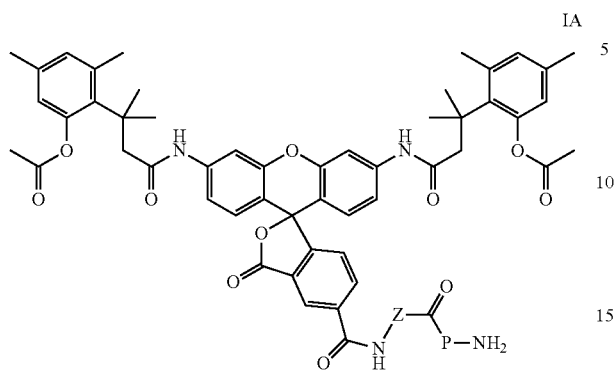
wherein Z is selected from the group consisting of substituted or unsubstituted C1 to C10 alkylene and substituted or unsubstituted C1 to C10 heteroalkylene, or when taken together with the NH and C=O moieties bonded thereto is an amino acid linker comprising from 1 to about 20 amino acids.
* * * * *

SEQUENCE LISTING

<160> NUMBER OF SEQ ID NOS: 122

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, Asn, Ala, Ile, Gly, Val, Pro, Phe or Tyr
<220> FEATURE:
<221> NAME/KEY: MOD_RES
<222> LOCATION: (2)..(2)
<223> OTHER INFORMATION: Pro, Ser, Glu, Gly, Lys, Ala, Asp, Val or Leu
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly
<220> FEATURE:
<221> NAME/KEY: MOD_RES
<222> LOCATION: (4)..(4)
<223> OTHER INFORMATION: Thr, Ala, Lys, Gly, Ser, Tyr, Glu, Met, Val or
      Leu
<220> FEATURE:
<221> NAME/KEY: MOD_RES
<222> LOCATION: (5)..(5)
<223> OTHER INFORMATION: Gly, Ala, Ser, Asp, Asn, Val, Gln, Glu, Lys or
      Pro

<400> SEQUENCE: 1

Xaa Xaa Xaa Xaa Xaa
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Pro Glu Thr Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any naturally occurring amino acid

<400> SEQUENCE: 3

Leu Pro Xaa Thr Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 4

Asn Pro Gln Thr Asn
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 5

Leu Pro Gln Thr Xaa Glu
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Pro Lys Thr Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Pro Asn Thr Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Pro Gln Thr Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Pro Ala Thr Gly
1               5
```

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Pro Asn Thr Ala
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Ala Glu Thr Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly
<220> FEATURE:
<221> NAME/KEY: MOD_RES
<222> LOCATION: (5)..(5)
<223> OTHER INFORMATION: Gly, Ala, Ser, Asp, Asn, Val, Gln, Glu, Lys or
      Pro

<400> SEQUENCE: 12

Leu Pro Xaa Thr Xaa
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly

<400> SEQUENCE: 13

Leu Pro Xaa Thr Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly
<220> FEATURE:
<221> NAME/KEY: MOD_RES
<222> LOCATION: (4)..(4)
<223> OTHER INFORMATION: Thr, Ala, Lys, Gly, Ser, Tyr, Glu, Met, Val or
      Leu

<400> SEQUENCE: 14

Leu Pro Xaa Xaa Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly

<400> SEQUENCE: 15

Leu Pro Xaa Ala Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly

<400> SEQUENCE: 16

Leu Pro Xaa Thr Ser
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly

<400> SEQUENCE: 17

Leu Pro Xaa Thr Asn
1               5

<210> SEQ ID NO 18
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly

<400> SEQUENCE: 18

Leu Ala Xaa Thr Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly

<400> SEQUENCE: 19

Leu Ser Xaa Thr Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly

<400> SEQUENCE: 20

Ile Pro Xaa Thr Gly
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly

<400> SEQUENCE: 21

Phe Pro Xaa Thr Gly
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: Lys, Ala, Asn, Gln, Glu, Thr, Pro, Ser, His,
      Asp, Ile, Arg, Val, Met, Phe, Leu, Tyr or Gly

<400> SEQUENCE: 22

Leu Pro Xaa Thr Ala
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Lys Lys Glu Lys
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Phe Pro Lys Thr Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Phe Pro Gln Thr Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Phe Pro Ser Thr Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Pro Asp Thr Ala
```

```
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ile Pro Ala Leu Gly
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ile Pro Asp Thr Gly
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Pro Glu Thr Gly
1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ile Pro Lys Thr Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ile Pro Met Thr Gly
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
              peptide

<400> SEQUENCE: 33

Ile Pro Asn Thr Gly
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Pro Gln Thr Gly
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ile Pro Arg Thr Gly
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ile Val Lys Thr Gly
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Ala Ala Thr Gly
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Ala Asp Thr Gly
1               5

<210> SEQ ID NO 39
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Ala His Thr Gly
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Ala Phe Thr Gly
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Ala Lys Thr Gly
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Ala Leu Thr Gly
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Ala Asn Thr Gly
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44
```

```
Leu Ala Arg Thr Gly
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Leu Ala Ser Thr Gly
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Ala Tyr Thr Gly
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Ala Glu Thr Pro
1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Glu Lys Thr Asn
1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Gly Ala Thr Gly
1               5

<210> SEQ ID NO 50
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 50

Leu Gly Asn Thr Gly
1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Leu Lys Thr Gly
1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Pro Ala Ala Gly
1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Pro Glu Ala Gly
1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Pro His Ala Gly
1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Pro Lys Ala Gly
1               5
```

```
<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Pro Leu Ala Gly
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Pro Asn Ala Gly
1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Pro Gln Ala Gly
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Pro Ser Ala Gly
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Pro Thr Ala Gly
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61
```

Leu Pro Lys Ala Asn
1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Leu Pro Glu Lys Gly
1               5

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Pro Ala Leu Gly
1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Pro Gln Met Asn
1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Pro Asp Thr Ala
1               5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Pro Glu Thr Ala
1               5

<210> SEQ ID NO 67
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 67

Leu Pro Lys Thr Ala
1               5

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Leu Pro Phe Ser Gly
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Leu Pro Ser Ser Gly
1               5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Leu Pro Gln Thr Asp
1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Leu Pro Asp Thr Gly
1               5

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Pro Glu Thr
1
```

```
<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Pro Phe Thr Gly
1               5

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Leu Pro Gly Thr Gly
1               5

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Pro His Thr Gly
1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Pro Ile Thr Gly
1               5

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Pro Leu Thr Gly
1               5

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 78

Leu Pro Met Thr Gly
1               5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Pro Arg Thr Gly
1               5

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Leu Pro Ser Thr Gly
1               5

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Leu Pro Thr Thr Gly
1               5

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Pro Val Thr Gly
1               5

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Leu Pro Tyr Thr Gly
1               5

<210> SEQ ID NO 84
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 84

Leu Pro Lys Thr Asn
1               5

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Pro Met Thr Asn
1               5

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Leu Pro Asn Thr Asn
1               5

<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Leu Pro Gln Thr Asn
1               5

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Leu Pro Thr Thr Asn
1               5

<210> SEQ ID NO 89
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Leu Pro Asp Thr Ser
1               5
```

```
<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Leu Pro Lys Thr Ser
1               5

<210> SEQ ID NO 91
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Leu Pro Asn Thr Ser
1               5

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Leu Pro Gln Thr Ser
1               5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Leu Pro Ser Thr Ser
1               5

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Leu Pro Glu Thr Val
1               5

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 95

Leu Pro Ile Val Gly
1               5

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Leu Pro Ile Tyr Ser
1               5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Leu Ser Asn Thr Gly
1               5

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Leu Ser Ser Thr Gly
1               5

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Leu Ser Phe Thr Gly
1               5

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Asn Ala Lys Thr Asn
1               5

<210> SEQ ID NO 101
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Asn Ala Lys Thr Ser
1               5

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Asn Lys Lys Ser Ala
1               5

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asn Pro Lys Thr Gly
1               5

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asn Pro Gln Thr Gly
1               5

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asn Pro Thr Lys Gln
1               5

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asn Asp Thr Ala Val
```

```
<210> SEQ ID NO 107
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Asn Pro Lys Ser Ser
1               5

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asn Ser Lys Thr Ala
1               5

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Pro Glu Thr Gly Glu
1               5

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Pro Lys Thr Gly Glu
1               5

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Val Pro Thr Gly Val
1               5

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 112

Val Ala Asn Thr Gly
1               5

<210> SEQ ID NO 113
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Val Pro Asp Thr Gly
1               5

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Val Pro Pro Thr Gly
1               5

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Tyr Pro Lys Thr Gly
1               5

<210> SEQ ID NO 116
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Tyr Pro Arg Thr Gly
1               5

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Lys Lys Lys Lys Lys Leu Pro Glu Thr Gly
1               5                   10

<210> SEQ ID NO 118

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Gly Gly Gly Gly Gly Gly Gly Leu Pro Glu Thr Gly
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Lys Gly Lys Gly Lys Leu Pro Glu Thr Gly
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Cys Gly Gly Gly Gly Gly Gly Leu Pro Glu Thr Gly
1               5                   10

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Cys Leu Pro Glu Thr Gly
1               5

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Gly Gly Gly Gly Leu Pro Glu Thr Gly
1               5                   10
```